United States Patent
Anderson et al.

(10) Patent No.: US 8,021,874 B2
(45) Date of Patent: Sep. 20, 2011

(54) VERY LONG CHAIN POLYUNSATURATED FATTY ACIDS, METHODS OF PRODUCTION, AND USES

(75) Inventors: Robert E. Anderson, Edmond, OK (US); Martin-Paul Agbaga, Oklahoma City, OK (US); Richard S. Brush, Midwest City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 18 days.

(21) Appl. No.: 12/361,163

(22) Filed: Jan. 28, 2009

(65) Prior Publication Data

US 2009/0203787 A1 Aug. 13, 2009

Related U.S. Application Data

(60) Provisional application No. 61/062,579, filed on Jan. 28, 2008.

(51) Int. Cl.
- C12M 1/00 (2006.01)
- C12P 21/06 (2006.01)
- C12N 1/20 (2006.01)

(52) U.S. Cl. ............... 435/289.1; 435/69.1; 435/252.3; 435/23.1

(58) Field of Classification Search ............ None
See application file for complete search history.

(56) References Cited

U.S. PATENT DOCUMENTS

| | | | |
|---|---|---|---|
| 7,091,005 B2 | 8/2006 | Petrukhin et al. | |
| 7,179,620 B2 | 2/2007 | Petrukhin et al. | |
| 2004/0067226 A1* | 4/2004 | Petrukhin et al. | 424/94.5 |
| 2005/0089981 A1* | 4/2005 | Napier et al. | 435/193 |
| 2005/0262580 A1 | 11/2005 | Petrukhin et al. | |
| 2005/0273885 A1 | 12/2005 | Singh et al. | |
| 2006/0206963 A1 | 9/2006 | Voelker et al. | |
| 2007/0220634 A1 | 9/2007 | Metz | |

OTHER PUBLICATIONS

Li et al.; Int. J. Biol. Sci 2007, 3(2)120-128.*
Cameron et al. Int. J. Biol. Sci. 2007, 3(2)111-119.*
Lagali PS, et al., "Evolutionarily conserved ELOVL4 gene expression in the vertebrate retina", *Invest Ophthalmol Vis. Sci.* (Jul. 2003);44(7), pp. 2841-2850.
Mandal MN, et al., "characterization of mouse orthologue of ELOVL4: genomic organization and spatial and temporal expression", *Genomics* (Apr. 2004);83(4), pp. 626-635.
McMahon A, et al., "A Stargardt disease-3 mutation in the mouse Elovl4 gene causes retinal deficiency of C32-C36 acyl phosphatidylcholines", *FEBS Lett.* (Nov. 7, 2007);581(28), pp. 5459-5463.
Vasireddy V, et al., "Loss of functional ELOVL4 depletes very long-chain fatty acids (>or=C28) and the unique omega-O-acylceramides in skin leading to neonatal death", *Hum. Mol. Genet.* (Mar. 1, 2007);16(5), pp. 471-482.
Zhang XM, et al., "Elovl4 mRNA distribution in the developing mouse retina and phylogenetic conservation of Elovl4 genes", *Mol. Vis.* (Jul. 3, 2003);9, pp. 301-307.
Cameron et al, Essential role of Elov14 in very long chain fatty acid synthesis, skin permeability barrier function, and neonatal survival, International Journal of Biological Sciences, Feb. 6, 2007, pp. 111-119.
Agbaga et al., "Role of Stargardt-3 macular dystrophy protein (ELOVL4) in the biosynthesis of very long chain fatty acids" *PNAS*, vol. 105, No. 35 (Sep. 2, 2008) pp. 12843-12848.
Agbaga et al., "Role of Elovl4 Protein in the Biosynthesis of Docosahexaenoic Acid" *Retinal Degenerative Diseases, Advances in Experimental Medicine and Biology* 664 Ch. 27 (2010) pp. 233-242.
Jakobsson et al., "Fatty acid elongases in mammals: Their regulation and roles in metabolism" *Progress in Lipid Research*, vol. 45 (2006) pp. 237-249.
Leonard et al., "Elongation of long-chain fatty acids" *Progress in Lipid Research*, vol. 43, (2004) pp. 36-54.

* cited by examiner

*Primary Examiner* — Doug Schultz
(74) *Attorney, Agent, or Firm* — Dunlap Codding, P.C.

(57) ABSTRACT

The present invention relates to processes for production of Very Long Chain Polyunsaturated Fatty Acids (VLC-PUFAs). The present invention also relates to compositions (e.g., nutritional supplements and food products) containing such VLC-PUFAs. In one embodiment, the present invention is directed to methods for biosynthesis and production of the VLC-PUFAs described herein (particularly C28-C38 PUFAs, also referred to herein as supraenes or supraenoics) by the expression, in a production host cell, of the full or partial sequence(s) of Elovl4 DNA/mRNA nucleic acids or ELOVL4 protein sequences encoded thereby, from any species (prokaryotic or eukaryotic) for use in the biosynthesis, production, purification and utilization of VLC-PUFAs in particular by the elongation of C18-C26 saturated fatty acids and PUFAs. The composition of the invention comprises, in various embodiments, a dietary supplement, a food product, a pharmaceutical formulation, a humanized animal milk, an infant formula, a cosmetic item and a biodiesel fuel for example. A pharmaceutical formulation can include, but is not limited to: a drug for treatment of neurodegenerative disease, a retinal disorder, age related maculopathy, a fertility disorder, particularly regarding sperm or testes, or a skin disorder.

33 Claims, 7 Drawing Sheets

VERY LONG CHAIN POLYUNSATURATED FATTY ACIDS, METHODS OF PRODUCTION, AND USES

CROSS-REFERENCE TO RELATED APPLICATIONS

The present application claims the benefit under 35 U.S.C. 119(e) of U.S. Provisional Application Ser. No. 61/062,579, filed Jan. 28, 2008, the entirety of which is hereby expressly incorporated herein by reference.

STATEMENT REGARDING FEDERALLY SPONSORED RESEARCH OR DEVELOPMENT

The invention was made with government support under Contract Numbers EY004149, EY000871, EY012190, and RR017703 awarded by the National Institutes of Health. The government has certain rights in the invention.

BACKGROUND OF THE INVENTION

Very long chain polyunsaturated fatty acids (VLC-PUFAs), with their structurally unusual long hydrocarbon chains, are essential lipids that play important roles in certain biological systems that cannot be fulfilled by the more common shorter chain C16-C18 fatty acids[25]. Because of their very long chain structure, some VLC-PUFAs are able to span and reside within both leaflets of the lipid bilayer, thereby giving stability to highly curved cellular membranes such as those which surround nuclear pore complexes[25]. In photoreceptors, for example, the VLC-PUFAs are known to be associated with rhodopsin and play a role in regulation of phototransduction cascades[18,21]. Absence of these VLC-PUFAs appears to contribute to macular degeneration in autosomal dominant Stargardt macular dystrophy (STGD3, MIM600110)[18], for example.

Three independent mutations in exon six of the Elongation of Very Long chain fatty acids-4 (ELOVL4) gene are associated with STGD3[1,2]. These mutations have been shown to cause truncation and subsequent mislocalization and aggregation of the normal ELOVL4 protein product[3-5]. Based on sequence homology with a group of functional yeast genes and other mammalian ELOVLs, the ELOVL4 protein was predicted to be involved in elongation of very long chain fatty acids (VLCFAs)[1,4,6]. For example, the microsomal ELO1 (Ssc1) is responsible for elongation of 14:0 to 16:0[7,8]. ELO2 (Ssc2), ELO3 (Cig30), and ELOVL5 have been shown to be involved in elongation of saturated, monounsaturated, or polyunsaturated fatty acids from 18 to 26 carbons[8-10]. However, whether the ELOVL4 protein is involved in fatty acid elongation, and the specific step it may catalyze, has remained unknown[9,11]. Based on its high level of expression in retinal photoreceptor cells, and to lesser extents in brain, testis and skin, it was first hypothesized that ELOVL4 may be involved in the biosynthetic pathway of docosahexaenoic acid (22:6n3, DHA), the most abundant polyunsaturated fatty acid in the retina and the brain[1]. However, recent experiments carried out in our laboratory (unpublished data) and results obtained from ELOVL4 mutant mice[12-14] do not support this hypothesis.

Current reports establish ELOVL4 as an essential protein for growth and development as homozygous ELOVL4 knock-out or knock-in of ELOVL4 mutant genes results in neonatal lethality in mice[12-15]. The heterozygote knock-in mouse, in which the mutant human ELOVL4 gene has replaced one wild type copy, develops progressive photoreceptor degeneration similar to human STGD3, demonstrating its association with the function of photoreceptors[16]. Homozygous neonates exhibit scaly wrinkled skin due to severely compromised epidermal permeability barrier and die within hours of birth[12-15,17]. Lipid analysis of the epidermis from the homozygote ELOVL4 knock-out mice indicated a global reduction in very long chain saturated and hydroxy fatty acids longer than 26:0 in omega hydroxyl ceramides/glucosylceramides and free fatty acid fractions[12-15]. Also, mice with one normal gene replaced with a gene containing the STGD3 disease mutation had lower amounts of C32-C36 acyl phosphatidylcholines in their retinas[18]. Based on these findings it was proposed that the ELOVL4 protein functions in VLC-FA and/or VLC-PUFA biosynthesis[14,15,18]. However, none of the studies published prior hereto have provided direct evidence that ELOVL4 is an elongase. Rather, previous work has only shown that absence or reduced expression of ELOVL4 leads to a reduction in the levels of certain fatty acids. This result could have several explanations not related to elongase activity. For example, ELOVL4 protein could provide some co-factor necessary for VLC-FA/PUFA synthesis or ELOVL4 protein could support activity of a cellular organelle necessary for VLC-FA/PUFA synthesis.

Moreover, research into the VLC-PUFA class of fatty acids has been restricted due to the unavailability of these fatty acids, and their use in commercial formulations and compositions has not been feasible due to the lack of known processes for synthesizing them. It is to the development of such synthetic methods and the compositions and uses of VLC-PUFAs produced therefrom, that the present invention is directed.

SUMMARY OF THE INVENTION

The present invention relates to processes for production of Very Long Chain Polyunsaturated Fatty Acids (VLC-PUFAs). The present invention also relates to compositions (e.g., nutritional supplements and food products) containing such VLC-PUFAs. In one embodiment, the present invention is directed to methods for biosynthesis and production of the VLC-PUFAs described herein (particularly C28-C38 PUFAs, also referred to herein as supraenes or supraenoics) by the expression, in a production host cell, of the full or partial sequence(s) of ELOVL4 DNA/mRNA nucleic acids or ELOVL4 protein sequences encoded thereby, from any species (prokaryotic or eukaryotic) for use in the biosynthesis, production, purification and utilization of VLC-PUFAs in particular by the elongation of C18-C26 saturated fatty acids and PUFAs. The composition of the invention comprises, in various embodiments, a dietary supplement, a food product, a pharmaceutical formulation, a humanized animal milk, an infant formula and a cosmetic item for example. A pharmaceutical formulation can include, but is not limited to: a drug for treatment of neurodegenerative disease, a retinal disorder, age related maculopathy, a fertility disorder particularly regarding sperm or testes, or a skin disorder.

The processes of the present invention include, but are not limited to, the use of any eukaryotic, prokaryotic or viral promoter(s) or enhancer(s) element known by persons of ordinary skill in the art to drive the production of expression of the ELOVL4 genes or proteins in host production cells such as algae, bacteria, yeast, plant, insect, worm, and mammalian cells. Cells are preferably transduced, infected, transfected, or otherwise transformed with the Elovl4 gene (or other similar sequences defined herein) and have genes for the expression of enzymes for elongating C18-C26 fatty acids and are grown in the presence of specific n3 and/or n6 fatty acid precursors (including but not limited to 18:3n3, 20:5n3, 22:5n3, 22:6n3, 18:2n6, 20:4n6, 22:4n6, 22:5n6, 24:5n3, 24:6n3, 24:4n6, 26:5n3, 26:6n3, 26:7n3, 26:5n6, or 26:6n6).

DETAILED DESCRIPTION OF THE INVENTION

Figure 1A:
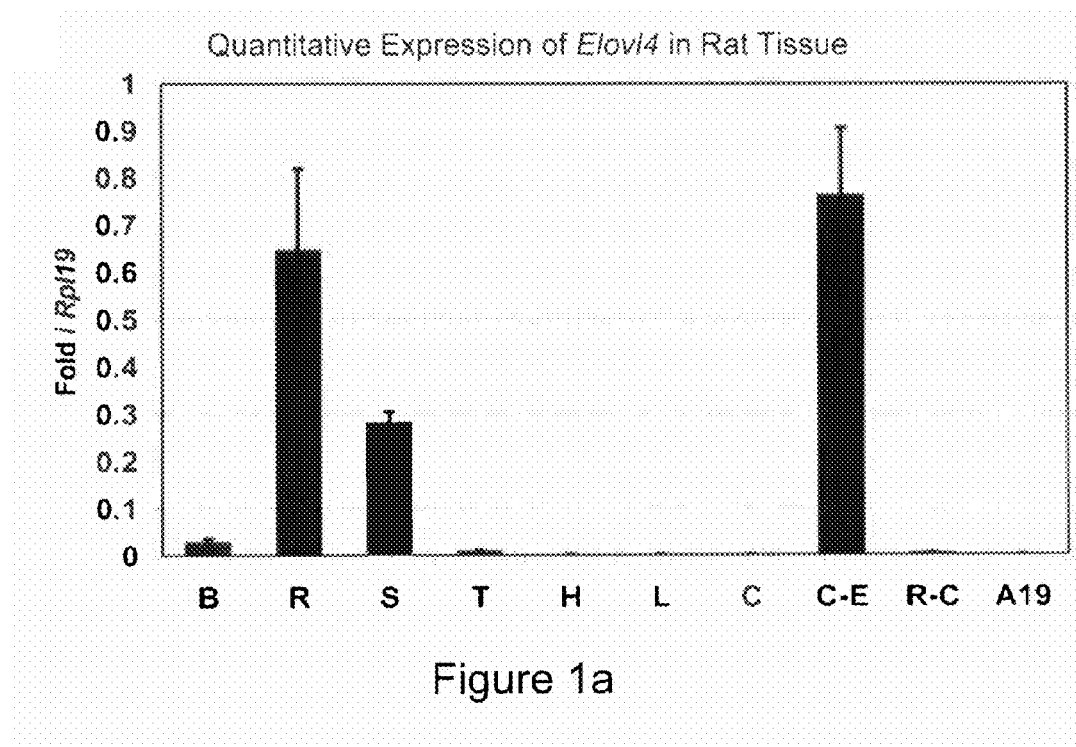
FIG. 1: Adenovirus efficiently transfers ELOVL4 protein to rat cardiac myocytes and ARPE-19 cells. (a) Expression values are determined by qRT-PCR and presented over the expression of house-keeping gene Rpl 19. B, brain; R, retina; S, skin; T, testis; L, liver; H, heart; C, cardiomyocytes; C-E, cardiomyocytes transduced with Elovl4; A19, ARPE19; R-C, RPE-Choroid. (b) Immunofluorescent images showing efficient adenoviral gene transfer in cardiac myocytes top row and ARPE-19 cells (middle row) infected with Ad5-mELOVL4 and cardiac myocytes infected with Ad5-GFP (bottom row); these are stained for mouse ELOVL4 (top and middle rows) and GFP protein (bottom row) 24 h post infection. The column on the left represents nuclei stain for DAPI (4',6-diamidino-2-phenylindole). The middle column represents ELOVL4 protein stains. The column on the right represents merged images from left and middle columns. Arrows represent some non-infected cells that do not express ELOVL4 or GFP proteins. c) Western blots showing ELOVL4 and GFP expression in transduced and non-transduced cells. Lanes: 1. myocytes non-transfected; 2. myocytes+Ad5-mELOVL4 24 h treatment; 3. myocytes+Ad5-mELOVL4 72 h treatment; 4. myocytes+Ad5-GFP 24 h treatment; 5. myocytes+Ad5-GFP 72 h treatment.

Very Long Chain Polyunsaturated Fatty Acids (VLC-PUFAs) having carbon chains of C28 to C40, while found in a number of species and organs therein (e.g., testes, retinas, brain, and sperm), are present in extremely small quantities. Prior to the present work, there have been no methods available for synthetically producing these VLC-PUFAs (much less in commercial quantities). In order to obtain even minute µg quantities of these VLC-PUFAs, they must be extracted from natural sources such as bovine retinas. As a result, research into C28-C38 VLC-PUFAs has been limited, and means for commercial production thereof have been non-existent. For example, ten bovine retinas typically yield roughly 500 µg of mixed VLC-PUFAs. The process involves discontinuous sucrose centrifugation to separate the photoreceptor outer segments (where the VLC-PUFAs are concentrated) from the rest of the retina, total lipid extraction to isolate lipids from the outer segments, derivatization to hydrolyze the lipids and generate fatty acid methyl esters (FAME), silver nitrate TLC to separate the VLC-PUFAs from undesired fatty acids, and reverse-phase TLC to further purify the VLC-PUFAs. This is a very time-consuming and labor intensive process to obtain only a very small quantity of VLC-PUFAs. Having a means of generating and obtaining large amounts of these VLC-PUFAs as contemplated and described herein is not only novel but is greatly desired.

In the present work, it has been established that ELOVL4 protein encoded by the Elovl4 gene catalyzes or co-catalyzes production of VLC-PUFAs by elongation of shorter chain (C18-C26) fatty acids. Based on this work, we have invented recombinant processes for synthetically producing C28-C38 VLC-PUFAs in significant quantity for use in purified compositions as well as in commercial compositions for use as nutritional formulas and supplements and as therapeutics for various diseases, disorders and conditions.

The term Very Long Chain Polyunsaturated Fatty Acid as used herein, generally refers to any polyunsaturated fatty acid or source thereof, having at least 28 carbon atoms per chain and having 3 or more carbon:carbon double bonds, including n3 (ω-3) and n6 (ω-6) polyunsaturated fatty acids.

More particularly, the PUFAs referred to herein are preferably polyunsaturated fatty acids with a carbon chain length of at least 28 carbons, or at least 30 carbons, or at least 32 carbons, or at least 34, or at least 36, or at least 38 carbons, or even 40 carbons, with at least 3 or more double bonds, or 4 or more, or 5 or more, or 6 or more double bonds, wherein all double bonds are preferably in the cis configuration. In a preferred embodiment, the present invention comprises methods of producing VLC-PUFAs and VLC-PUFA compositions produced therefrom, preferably recombinantly. Note that where the term "C28-C38" is used, this is intended to also include reference to C40 PUFAs, i.e., polyunsaturated fatty acids comprising a 40 carbon chain.

Examples disclosed herein describe and demonstrate specific embodiments within the scope of the present invention. The examples are given solely for the purpose of illustration and are not to be construed as limitations of the present invention, as many variations thereof are possible without departing from the spirit and scope of the invention. All exemplified amounts are weight percentages based upon the total weight of the composition, unless otherwise specified.

Two main families of polyunsaturated fatty acids (PUFAs) are the ω3 (n3) fatty acids, exemplified by eicosapentaenoic acid (EPA), and the ω6 (n6) fatty acids, exemplified by arachidonic acid (ARA). PUFAs are important components of the plasma membrane of the cell, where they may be found in such forms as phospholipids and triglycerides. PUFAs are necessary for proper development, particularly in the developing infant brain, and for tissue formation and repair. PUFAs also serve as precursors to other molecules of importance in human beings and animals, including the prostacyclins, eicosanoids, leukotrienes and prostaglandins. Four major long chain PUFAs of importance include docosahexaenoic acid (DHA) and EPA, which are primarily found in different types of fish oil, gamma-linolenic acid (GLA), which is found in the seeds of a number of plants, and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland. GLA, ARA, EPA and SDA are themselves, or are dietary precursors to, important long chain fatty acids involved in prostaglandin synthesis, in treatment of heart disease, and in development of brain tissue.

Several disorders respond to treatment with fatty acids. For example, dietary supplementation with PUFAs has been shown to reduce the rate of restenosis after angioplasty. Fish oil supplements have been shown to improve symptoms of inflammation and rheumatoid arthritis, and PUFAs have been suggested as treatments for asthma and psoriasis. Evidence indicates that PUFAs may be involved in calcium metabolism, suggesting that PUFAs may be useful in the treatment or prevention of osteoporosis and of kidney or urinary tract stones.

However, in spite of the evidence of the requirements of VLC-PUFAs for various developmental and physiologic processes, commercially-available dietary supplements, nutritional formulations, and pharmaceutical formulations which contain C28-C38 VLC-PUFAs are not currently available since, prior to the current work, there has been no known method of synthesizing such VLC-PUFAs.

Novel methods are thus provided herein for the production of VLC-PUFAs. Novel expression systems using nucleic acids encoding ELOVL4 protein and/or polypeptides having ELOVL4 elongase activity are described. The methods involve growing a host microorganism, cell, plant, or animal which contains and expresses one or more transgenes encoding ELOVL4 protein and/or a polypeptide having ELOVL4 elongase activity. The methods of the invention, unless otherwise specified, generally result in the production of a mixture of VLC-PUFAs of C28-C38 chain length, although production of specific VLC-PUFAs can be enhanced by exposing the host organism to specific precursor substrates or by the use of host organisms having suites of particular fatty acid synthesizing genes.

Examples of VLC-PUFAs which may be used or manufactured in the present invention for use in any composition described or contemplated herein include all or any combination of the following (but are not limited thereto):

(1) All (C28-C40) n-3 fatty acid families; including but not limited to: 28:4n3, 28:5n3, 28:6n3, 28:7n3, 28:8n3, 30:4n3, 30:5n3, 30:6n3, 30:7n3, 30:8n3, 32:4n3 32:5n3, 32:6n3, 32:7n3, 32:8n3, 34:4n3, 34:5n3, 34:6n3, 34:7n3, 34:8n3, 36:4n3, 36:5n3, 36:6n3, 36:7n3, 36:8n3, 38:4n3, 38:5n3, 38:6n3; 38:7n3, 38:8n3, 40:4n3, 40:5n3, 40:6n3, 40:7n3, and 40:8n3, and (2) All (C28-C40) n-6 fatty acid families; including but not limited to: 28:3n6, 28:4n6, 28:5n6, 28:6n6, 28:7n6, 30:3n6, 30:4n6, 30:5n6, 30:6n6, 30:7n6, 32:3n6, 32:4n6, 32:5n6, 32:6n6, 32:7n6, 34:3n6, 34:4n6, 34:5n6, 34:6n6, 34:7n6, 36:3n6, 36:4n6, 36:5n6, 36:6n6, 36:7n6, 38:3n6, 38:4n6, 38:5n6, 38:6n6, 38:7n6, 40:3n6, 40:4n6, 40:5n6, 40:6n6, and 40:7n6.

In a preferred embodiment, a host cell transfected with a nucleic acid sequence comprising an Elovl4 gene (such as, but not limited to, SEQ ID NO.: 1, 3, 5, 7, 9, 11, 13, 15 or 17) is provided. The host cell is able to produce the ELOVL4 protein (such as, but not limited to, SEQ ID NO.:2, 4, 6, 8, 10, 12, 14, 16 or 18) which is used within the transfected host cell to produce a mixture of VLC-PUFAs, such as are described elsewhere herein. In another embodiment, the nucleic acid may be an isolated nucleic acid comprising a sequence which anneals to one or more of nucleotide sequences SEQ ID NO.:1, 3, 5, 7, 9, 11, 13, 15 or 17, and which encodes an amino acid sequence having ELOVL4 activity such as SEQ ID NO.: 2, 4, 6, 8, 10, 12, 14, 16 or 18, or proteins homologous thereto which have conservative substitutions and which have ELOVL4 activity. The invention also provides a host cell having an isolated nucleic acid sequence able to hybridize to an ELOVL4 nucleotide sequence as described herein and which has at least 90% identity thereto, and more preferably 95%, 96%, 97%, 98%, or 99% identity. As used herein, unless otherwise specified, reference to a percent (%) identity refers to an evaluation of homology which is performed using software including, but not limited to, a BLAST 2.0 Basic BLAST homology search. The host cell of the present invention may comprise a nucleic acid construct comprising an Elovl4 gene, as described herein, which is operably linked to a promoter which is functional in the host cell. In one embodiment of the present invention, the recombinant Elovl4 nucleic acid molecule of the host cell is operatively linked to at least one transcription control sequence.

The host cell or organism is either eukaryotic or prokaryotic. Examples of eukaryotic host cells or organisms are those selected from the group consisting of a mammalian cell, an avian cell, a protozoan, an insect cell, a fungal cell such as a yeast, such as *Sacchoromyces* sp., and an algae cell, such as a marine algae. Preferred prokaryotic cells include those selected from the group consisting of a bacteria, particularly *E. coli*, a cyanobacteria, cells which contain a bacteriophage, and/or a virus.

The host cells or organisms of the invention preferably comprise nucleic acids which encode enzymes necessary for production of fatty acid precursors for the production of the C28-C38 VLC-PUFAs such as, but not limited to, 18:3n3, 20:5n3, 22:5n3, 22:6n3, 18:2n6, 20:4n6, 22:4n6, or 22:5n6 or C24 or C26 fatty acids. In a preferred embodiment, the host cells synthesize C26 fatty acids as compared to an untransformed host cell which is substantially devoid of a DNA sequence which encodes enzymes necessary for production of C26 fatty acids. Alternatively, the C26 substrate (or other PUFAs<C26) for said polypeptide may be exogenously supplied.

Preferred microbial strains used herein, as noted elsewhere herein, may be chosen from the group consisting of: bacteria, algae, fungi, protozoa or protists, but most preferably from the eukaryotic microbes consisting of algae, fingi, protozoa and protists. These microbes are preferably capable of growth and production of the bioactive compounds containing two or more unsaturated bonds at temperatures greater than about 15° C., more preferably greater than about 20° C., even more preferably greater than about 25° C., and most preferably greater than about 30° C. Microorganisms contemplated as host cells for use in producing the VLC-PUFAs of the present invention include, but are not limited to, those belonging to the genera *Mortierella, Conidiobolus, Pythium, Phytophathora, Penicillium, Porphyridium, Coidosporium,*

*Mucor, Fusarium, Aspergillus, Rhodotorula*, and *Entomophthora*, and particularly *Porphyridium cruentum, Mortierella elongata, Mortierella exigua, Mortierella hygrophila, Mortierella ramanniana*, var. *angulispora*, and *Mortierella alpina*, and *Mucor circinelloides* and *Mucor javanicus*. Preferred fungi which may be used as host cells are of the order Mucorales. For example, the fungus may be of the genus *Mortierella, Phycomyce, Blakeslea*, or *Aspergillus*. A preferred yeast germ is of the genus *Pichia*, such as *Pichia ciferrii* and *Pichia pastoris*. Examples of bacteria include the genus *Propionibacterium*. Examples of algae host cells include a dinoflagellate and/or belongs to the genus *Crypthecodinium* such as *Crypthecodinium cohnii*.

The present invention contemplates a host cell having a DNA sequence which encodes an amino acid sequence having the elongase activity (i.e., having the ability to elongate C26 fatty acids) of an ELOVL4 enzyme, wherein the DNA sequence encoding the amino acid sequence is capable of hybridizing under moderate, high, or very high stringency conditions (described below) to or with a nucleic acid molecule encoding an ELOVL4 protein as contemplated herein. Preferably, the nucleic acid sequence encoding the protein having ELOVL4 activity hybridizes under moderate, high or very high stringency conditions to the nucleic acid sequence comprising any one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17, or a complement thereof.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62).

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% to 95% nucleic acid sequence identity with the nucleic acid molecule being used to probe in the hybridization reaction (i.e., conditions permitting about 10% to 5% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids.

In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C., (more stringent), and even more preferably, between about 35° C. and about 45° C., (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

As used herein, a genetically modified plant may be used to produce VLC-PUFAs of the invention and can include any genetically modified plant including higher plants and particularly, any consumable plants or plants useful for producing a desired VLC-PUFA of the present invention. Such a genetically modified plant has a genome which is modified (i.e., mutated or changed) from its normal (i.e., wild-type or naturally occurring) form such that the desired result is achieved (i.e., VLC-PUFA production). Genetic modification of a plant can be accomplished using conventional molecular genetic techniques. Methods for producing a transgenic plant, wherein a recombinant nucleic acid molecule encoding a desired amino acid sequence is incorporated into the genome of the plant, are known in the art. A preferred plant to genetically modify according to the present invention is preferably a plant suitable for consumption by animals, including humans.

Preferred plants to genetically modify according to the present invention (i.e., plant host cells) include, but are not limited to any higher plants, and particularly consumable plants, including crop plants and especially plants used for their oils. Such plants can include, for example: canola, soybeans, rapeseed, linseed, corn, safflowers, sunflowers and tobacco. Other preferred plants include those plants that are known to produce compounds used as pharmaceutical agents, flavoring agents, neutraceutical agents, functional food ingredients or cosmetically active agents or plants that are genetically engineered to produce these compounds/agents.

Examples of oil seed plants, which could be transfected with an Elovl4 gene as contemplated herein and methods of their transfection are described for example in U.S. Pat. No. 7,179,647.

As described above, in one embodiment of the present invention, a genetically modified prokaryotic microorganism, eukaryotic microbes or plant includes a microorganism or plant which has an enhanced ability to synthesize VLC-PUFA molecules (products) or which has a newly introduced ability to synthesize specific VLC-PUFAs. According to the present invention, "an enhanced ability to synthesize" a product refers to any enhancement, or up-regulation, in a pathway related to the synthesis of the product such that the microorganism or plant produces an increased amount of the VLC-PUFA (including any production of the product where there was none before) as compared to the wild-type microorganism or plant, cultured or grown, under the same conditions. Methods to produce such genetically modified organisms have been described in detail elsewhere herein and in the art.

In the method of production of VLC-PUFAs of the present invention, the genetically modified host cells or organisms are cultured or grown in a suitable medium, under conditions effective to produce the VLC-PUFAs. An appropriate, or effective, medium refers to any medium in which a genetically modified host cell or organism (also referred to herein as micro-organism) of the present invention, when cultured, is capable of producing the VLC-PUFAs. Such a medium is typically an aqueous medium comprising assimilable carbon, nitrogen and phosphate sources. Such a medium can also include appropriate salts, minerals, metals and other nutrients and precursor fatty acids. Microorganisms of the present invention can be cultured in conventional fermentation or growth bioreactors. The microorganisms can be cultured by any fermentation process which includes, but is not limited to, batch, fed-batch, cell recycle, and continuous fermentation. Preferred growth conditions for potential host microorganisms according to the present invention are well known in the art. The VLC-PUFAs produced by the genetically modified microorganism can be recovered from the fermentation medium using conventional separation and purification techniques as described elsewhere herein. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, membrane separation, electrodialysis, reverse osmosis, distillation, chemical derivatization and crystallization. Alternatively, microorganisms producing the VLC-PUFAs, or extracts and various fractions thereof, can be used without removal of the microorganism components from the product.

In the method for production of desired bioactive compounds of the present invention, a genetically modified plant is cultured in a fermentation medium or grown in a suitable medium such as soil. An appropriate, or effective, fermentation medium has been discussed in detail elsewhere herein. A suitable growth medium for higher plants includes any growth medium for plants, including, but not limited to, soil, sand, any other particulate media that support root growth (e.g. vermiculite, perlite, etc.) or hydroponic culture, as well as suitable light, water and nutritional supplements which optimize the growth of the higher plant. The genetically modified plants of the present invention are engineered to produce significant quantities of the VLC-PUFAs. The compounds can be recovered through purification processes which extract the compounds from the plant. In a preferred embodiment, the compound is recovered by harvesting the plant. In this embodiment, the plant can be consumed in its natural state or further processed into consumable products.

Preferably, VLC-PUFAs of the invention are produced by the genetically modified host cell or organism in a dry weight amount that is greater than about 1%, and preferably greater than about 2%, and more preferably greater than about 5%, and more preferably greater than about 10%, and more preferably greater than about 15%, and more preferably greater than about 20%, and more preferably greater than about 25%, and more preferably greater than about 30%, and more preferably greater than about 40%, and more preferably greater than about 50%, and even more preferably greater than about 60% or 75% of the dry weight of the microorganism. Yet another embodiment of the present invention relates to a method to produce a humanized animal milk product. This method includes the steps of genetically modifying milk-producing cells of a milk-producing animal with at least one recombinant nucleic acid molecule comprising a nucleic acid sequence encoding at least one biologically active domain of an ELOVL4 protein.

Methods to genetically modify a host cell and to produce a genetically modified non-human, milk-producing animal, are known in the art. Examples of host animals to modify include, but are not limited to, cattle, sheep, pigs, goats, and yaks, which are amenable to genetic manipulation and cloning for rapid expansion of a transgene expressing population. For animals, Elovl4 transgenes can be adapted for expression in target organelles, tissues and body fluids through modification of the gene regulatory regions. Of particular interest is the production of VLC-PUFAs in the breast milk of the host animal.

Viral constructs from Adeno-associated virus (AAV), lentiviral vectors and retroviral vectors with different kinds of promoters can be used to express ELOVL4 in the host cells contemplated herein. The host cells contemplated herein can be transiently or stably transfected with expression vectors with different promoters to drive the expression of the ELOVL4 protein. ELOVL4 can be over-expressed in the host cells contemplated herein as recombinant or pure proteins that can be secreted or purified as pure or substantially pure ELOVL4 proteins. The pure or substantially pure proteins can be used with cell-free or tissue-free homogenates or in combination with other ELOVLs to make the VLC-PUFAs in the presence of C18-C26 n-3 or n-6 fatty acid precursors, such as but not limited to, 18:3n3, 20:5n3, 22:5n3, 22:6n3, 18:2n6, 18:3n6, 20:4n6, 22:4n6, 22:5n6, 24:5n3, 24:6n3, 24:4n6, 26:5n3, 26:6n3, 26:7n3, 26:5n6, or 26:6n6 or other described herein. Generally, n3 precursor substrates (such as 18:3n3, 20:5n3 or 22:5n3) will substantially lead to n3 products, and n6 substrates (e.g., 18:2n6, 20:4n6) will substantially lead to n6 products. In order to custom tailor production of specific VLC-PUFAs in the host cell or organism, a specific combination of fatty acid precursors (as described herein) and fatty acid metabolism enzymes (other than ELOVL4) must be present. Such enzymes for elongation of VLC fatty acids are known in the art.

As noted above, examples of DNA sequences for the Elovl4 gene from different species that could be used in host cells for making the n-3 or n-6 VLC-PUFAs (Supranenes, Supraenoics) of the present invention, include, but are not limited to, SEQ ID NOs:1, 3, 5, 7, 9, 11, 13, 15, and 17. Protein sequences encoded thereby include SEQ ID NOs:2, 4, 6, 8, 10, 12, 14, 16, and 18, respectively.

In one embodiment, the Elovl4 genes contemplated herein (including any appropriate or effective Elovl4 gene not shown herein) can be transduced, transfected or infected into host cells for production of C28-C38 PUFAs in accordance with the present invention. Examples of host cells and organisms that can be genetically engineered to be used to produce the fatty acids in the methods of the present invention include, but are not limited to, those described for example in U.S. Pat. Nos. 5,407,957; 5,492,938; 5,550,156; 5,711,983; 6,027,900; 6,812,009; 6,977,167; 7,001,772; 7,011,962; 7,022,512; 7,179,647; 7,195,791; 7,252,979; and 7,256,022. Preferably each host cell or organism used in the present invention is capable of endogenously producing C18, C20, C22, C24, and/or C26 fatty acid precursors (saturated or unsaturated) for production of the C28-C38 fatty acids of the present invention.

Recovery of the VLC-PUFAs recombinantly produced in the host organisms can be accomplished by any suitable method, including numerous methods known in the art. For example, recovery can include the following method. Harvested cells (fresh or dried) can be ruptured using techniques known to those in the art. Lipids can then be extracted from the cells by any suitable means, such as by supercritical fluid extraction, or by extraction with solvents such as chloroform, hexane, methylene chloride, methanol, isopropanol, ethyl acetate, and the like, and the extract evaporated under reduced pressure to produce a sample of concentrated lipid material. The VLC-PUFAs can be further separated from other lipids by chilling a fatty acid composition such that the saturated fatty acids in the composition precipitate out while the PUFAs remains in solution. The lipids can then be recovered from the extract.

The host organisms used to produce the VLC-PUFAs herein can also be broken or lysed and the lipids recovered into edible oil using standard methods known in the art. The recovered oils can be refined by well-known processes routinely employed to refine vegetable oils (e.g., chemical or physical refining). These refining processes remove impurities from recovered oils before they are used or sold as edible oils. The refining process consists of a series of processes to degum, bleach, filter, deodorize and polish the recovered oils. After refining, the oils can be used directly as a feed or food additive to produce VLC-PUFA-enriched products. Alternatively, the oil can be further processed and purified as outlined herein and then used in the applications as described herein. The purified oil extract of the present invention preferably comprises a VLC-PUFA content of 0.1-99%, for example, >25%, >50%, >60%, >75%, >85%, >90%, $\geq$92%, more preferably a content $\geq$94%, and more preferably $\geq$95% and most preferably at least 96%, 97%, 98%, or 99%. Individual VLC-PUFAs (e.g., 28-38:5n3, 28-38:6n3, 28-38:7n3, 28-38:8n3, 28-38:4n6, 28-38:5n6, 28-38:6n6, or 28-38:7n6) can be obtained in at least 50% purity or greater from a mixture of VLC-PUFAs. They can be further isolated and purified by selective metabolism as well as known chromatographic procedures.

As noted above, the present invention also relates to a method of isolating the VLC-PUFA-containing oil from host cell biomass, wherein the host biomass can be pretreated before extraction of the oil. Due to the relatively mild conditions of the pretreatment process, the thermo- and oxidation-sensitive PUFAs present in the oil may not be exposed to conditions causing degradation.

Thus, according to one aspect of the present invention, a process is provided for obtaining an oil comprising at least one VLC-PUFA from a host cell biomass (comprising organisms that have produced the VLC-PUFA), the process comprising:

a) providing, or obtaining, a biomass with a dry matter content of, for example, from 20 to 90%;
b) granulating the biomass into granular particles;
c) drying the granular particles to give dried granules; and
d) extracting or isolating the oil from the dried granules.

Preferably, the particulate granular form has an average dry matter content of from 30% to 70%. The dried granules resulting from (c) preferably have an average dry matter content of at least 80%.

In another aspect of the present invention there is provided a process for the isolation of one or more VLC-PUFA compounds from a host cell biomass, the process comprising:

a) culturing the host cells, e.g., microorganisms, in a fermentation broth under conditions whereby the compound is produced (by the host cells);
b) pasteurizing either the fermentation broth or a host cell biomass derived from the broth; and
c) extracting, isolating or recovering the VLC-PUFAs from the host cell biomass.

The pasteurization in (b) is intended to at least partially inactivate one or more PUFA-degrading substance(s) that may be present in the biomass or broth. Such substances can include proteins, such as enzymes (e.g. proteases). In particular, one is seeking to at least partially inactivate lipases, phospholipases and/or lipoxygenases. Preferably, this pasteurization takes place before granulating (or crumbling or kneading). Suitably, pasteurization is performed on the fermentation broth, although it can be performed on the host cell biomass obtained from the broth.

By pasteurization it is thought that at least some of the substances that can cause degradation of the compound (VLC-PUFA) can be avoided. This pasteurization may at least contribute to the high quality VLC-PUFAs that can be obtained by the present invention.

After pasteurization, but before extraction in (c), one may perform granulating (to give granular particles) and drying the granular particles as described above in stages (b) and (c) in the second aspect of the invention. Preferred features of one aspect of the invention are equally applicable, where appropriate, to other aspects.

In one process of the invention, host cell microorganisms are first grown or fermented under conditions that allow production of the VLC-PUFAs to occur. Such fermentation processes are well known in the art: the microorganism is usually fed with a carbon and nitrogen source, along with a number of additional chemicals or substances such as PUFA precursors that allow growth of the microorganism and/or production of the VLC-PUFA. The resulting material from fermentation (which is often called the broth) can then be filtered, or otherwise treated to remove at least part of the aqueous component. Suitably a large proportion of the water is removed, in order to obtain a biomass cake. The biomass at this stage preferably has a dry matter content of from 25% to 80%. The biomass can then be granulated into granular particles. This is preferably achieved by extrusion. However, whichever technique for granulation is chosen, it is preferable that cell disruption is either prevented or minimized. The granular particles can then be dried. The granules can significantly increase the efficiency of the subsequent drying step. The resulting (dried) granules are then particularly suitable for immersion or percolation extraction. The particle sizes of the granules can be adjusted for optimal drying and extraction additions.

Preferably, the VLC-PUFAs are extracted from the dried granules using a solvent. Any suitable solvent known to a person skilled in the art can be employed. However, suitably a non-polar solvent is used, for example hexane. It is also possible to use solvents in a super critical state, for example liquid carbon dioxide.

The process of the invention can enable a cost effective and efficient extraction of the VLC-PUFA oil, and provide an oil of a particularly high quality. For example, the dried granular form (of the host cell biomass) allows one to use the percolation extraction process, which is particularly efficient. In addition, the granules allow the use of a relatively low temperature for extraction, which does not necessarily decrease the yield of the VLC-PUFAs. Furthermore, the dried granules may require reduced amounts of solvent for the extraction process. An additional advantage is that the release of the used solvent from the biomass can be achieved more efficiently (this process is often referred to as desolventising toasting). All combinations of method or process steps as used herein can be performed in any order, unless otherwise specified or clearly implied to the contrary by the context in which the referenced combination is made.

Preferably, strains of host microorganisms, cells, plants or animals used herein are capable of producing a total VLC-PUFA content of at least about 5% of dry weight of the product derived therefrom, preferably at least about 10% of dry weight, and more preferably at least about 20% of dry weight. More preferred strains of host microorganisms produce at least about 30% dry weight of VLC-PUFAs, more preferably at least about 40% dry weight of VLC-PUFAs, and even more preferably at least about 50% dry weight of VLC-PUFAs.

In one embodiment of the present invention an oil recovered, such as by extraction, from the host organism contains at least about 20% dry weight of at least one type of VLC-PUFA contemplated herein. The biomass from which the oil of the invention is obtained can comprise, or originate from, any type of host organism able to produce a VLC-PUFA-containing oil, for example a bacterium, a yeast, a fungus, an algae (or a mixture thereof), an animal cell, or a plant cell.

The VLC-PUFA compositions of the present invention as produced herein can be used for example as dietary substitutes, as supplements of infant formulas, for patients undergoing intravenous feeding, or for preventing or treating malnutrition. For dietary supplementation, the purified VLC-PUFAs may be incorporated into cooking oils, fats or margarines formulated so that in normal use the recipient would receive a useful amount. The VLC-PUFAs may be used as, or in, pharmaceutical compositions.

The composition of the present invention may comprise a "food product" which refers to any product to be fed to a human or animals. Preferred food materials to be consumed by humans include infant formula and baby food. Preferred food materials to be consumed by domestic pets include dog and cat foods. The food product may be a livestock feed. The food product of the invention may comprise host organism biomass or the oil extracted therefrom. As described elsewhere herein, the VLC-PUFAs recovered from the biomass of the host organisms of the present invention can be combined with any animal food material, particularly food materials for humans or animals, or can be used alone as a therapeutic composition.

As noted elsewhere herein, the VLC-PUFAs of the invention can be added to foods for infants, such as infant formula and baby food. According to the present invention, an infant refers to infants in utero and to children less than about two years old, including, in particular, premature infants. Preferably, the VLC-PUFA produced using the present invention is used in a product comprising at least one of a food, a dietary supplement, a pharmaceutical formulation, a humanized animal milk, and an infant formula. It is also contemplated that the VLC-PUFAs of the present invention can be used in soaps, cosmetics, lotions, creams, oils, shampoos, and similar items produced by the cosmetic and skin care industry. The VLC-PUFAs of the present invention may be formulated into the composition as the free fatty acid or as a salt of the free fatty acid or as compounds or materials that can otherwise provide a source of such free fatty acids upon or following administration to the person, including phospholipids and glyceride esters (mono-, di-, tri-) of the polyunsaturated fatty acids. The compositions of the present invention comprise one or more of the C28-C38 PUFAs contemplated herein, or combinations thereof, alone or in further combination with other PUFAs such as linoleic acid, linolenic acid, ARA, DHA, DPA, and/or EPA. The concentration of C28-C38 VLC-PUFAs in the dietary and supplemental formulas of the present invention includes any concentration or amount which is safe for internal, topical, or commercial use.

The present invention further contemplates an oil comprising one or more C28-C38 VLC-PUFAs. The oil may be an extracted mixture of VLC-PUFAs comprising for example 0.1-99.9% of a C28 PUFA, and/or 0.1-99.9% of a C30 PUFA, and/or 0.1-99.9% of a C32 PUFA, and/or 0.1-99.9% of a C34 PUFA, and/or 0.1-99.9% of a C36 PUFA, and/or 0.1-99.9% of a C38 PUFA, and/or 0.1-99.9% of a C40 PUFA. In a preferred embodiment, the oil extract mixture is purified such that a single C28-C38 PUFA comprises at least 25%, or at least 50%, and more preferably 75%, or more preferably at least 95% of the total fatty acid content of the oil or mixture of PUFAs.

In one embodiment, a mixture of VLC-PUFAs derived from the host cell or microorganism will contain 0.1% to 99.9% of a C28:4n3, 5n3, 6n3, 7n3, 8n3, 3n6, 4n6, 5n6, 6n6, and/or 7n6; 0.1% to 99.9% of a C30:4n3, 5n3, 6n3, 7n3, 8n3, 3n6, 4n6, 5n6, 6n6, and/or 7n6; 0.1% to 99.9% of a C32:4n3, 5n3, 6n3, 7n3, 8n3, 3n6, 4n6, 5n6, 6n6, and/or 7n6; 0.1% to 99.9% of a C34:4n3, 5n3, 6n3, 7n3, 8n3, 3n6, 4n6, 5n6, 6n6, and/or 7n6; 0.1% to 99.9% of a C36:4n3, 5n3, 6n3, 7n3, 8n3, 3n6, 4n6, 5n6, 6n6, and/or 7n6; or 0.1% to 99.9% of a C38:4n3, 5n3, 6n3, 7n3, 8n3, 3n6, 4n6, 5n6, 6n6, and/or 7n6 PUFA.

Another preferred embodiment of the invention is a pharmaceutical composition comprising one or more of the C28-C38 PUFAs contemplated herein in a pharmaceutically acceptable carrier. Further contemplated is a nutritional composition comprising one or more of the C28-C38 PUFAs of the invention. The nutritional composition of the invention preferably is administered to a mammalian subject orally, parenterally or otherwise internally. A preferred composition of the invention for internal consumption is an infant formula or an oral dosage form for treatment or prevention of a disease condition. In a preferred embodiment, the nutritional compositions of the invention are in a liquid form or a solid form as discussed elsewhere herein. In one embodiment as a dietary supplement, the VLC-PUFAs are dissolved in a vegetable oil and supplied, for example, at 1 to 500 mg per day, or 10-250 mg per day. For commercial sale for research or other purposes, specific VLC-PUFAs can be supplied as a substantially pure substance (e.g., 99% pure) sealed under an inert gas such as nitrogen or argon and sold in amounts, for example, ranging from 1 mg to 1 gm, as free fatty acids, free fatty acid salts, or in whole lipid form.

Infant formulas of the invention typically contain proteins, carbohydrates, lipids, vitamins, minerals, and other nutrients, and are commercially available as reconstitutable powders, ready-to-feed liquids, and dilutable liquid concentrates.

Many nutritional formulas, especially infant formulas, commonly contain a variety of mid-chain and shorter chain PUFAs as part of the lipid component of the overall nutrient system, examples of which include linoleic acid, alpha-linolenic acid, eicosapentaenoic acid (EPA), arachidonic acid (ARA), decosahexaenoic acid (DHA), among others. Arachidonic and decosahexaenoic acids in particular are commonly found in many commercially available infant formulas such as ENFAMIL, ISOMIL, SIMILAC, and ADVANCE.

As such, the present invention in one embodiment is directed to methods of providing nutrition to an infant, toddler, child, or adult, said method comprising the administration or feeding a composition of the present invention to the infant, toddler, child, or adult as a nutritional formula or supplement as their sole, primary, or partial nutritional needs.

The compositions of the present invention may comprise protein, carbohydrate, and lipids, as well as the one or more VLC-PUFAs of the present invention, and may contain combinations of antioxidant carotenoids including lutein, lycopene, and beta-carotene. These and other elements of the nutritional formulas and corresponding methods of the present invention are described elsewhere herein and in the art. The compositions may further comprise vitamins, minerals, and electrolytes, and may potentially serve as the sole source of nutrition when provided in sufficient quantity.

It has been shown that infants benefit from consuming breast milk or formula containing docosahexaenoic acid (DHA; 22:6n3) and arachidonic acid (AA; 20:4n6) and related polyunsaturated fatty acids[32]. As a result, infant formula is now supplemented with such fatty acids. The brain and retina are two areas where VLC-PUFAs are found. Consequently, in one aspect, the invention contemplates dietary supplementation to infants and pregnant females with these VLC-PUFAs for aiding in neural development and function in infants.

When the composition is an adult formula, the protein component may comprise for example from about 10% to about 80% of the total caloric content of said nutritional formula; the carbohydrate component may comprise for example from about 10% to about 70% of the total caloric content of said nutritional formula; and the lipid component may comprise for example from about 5% to about 50% of the total caloric content of said nutritional formula. The nutritional formula may be in liquid or powder form. These ranges are provided as examples only, and are not intended to be limiting.

When the composition is a non-adult nutritional composition, the non-adult composition includes those embodiments in which the protein component may comprise for example from about 7.5% to about 25% of the total caloric content of the nutritional composition; the carbohydrate component may comprise for example from about 35% to about 50% of the total caloric content of the nutritional formula; and the lipid component may comprise for example from about 30% to about 60% of the total caloric content of the nutritional formula. These ranges are provided as examples only, and are not intended to be limiting.

Many different sources and types of carbohydrates, lipids, proteins, minerals and vitamins are known and can be used in the nutritional compositions of the present invention, provided that such nutrients are compatible with the added ingredients in the selected formula, are safe for their intended use, and do not otherwise unduly impair product performance.

Carbohydrates suitable for use in the nutritional compositions of the present invention can be simple or complex, lactose-containing or lactose-free, or combinations thereof, non-limiting examples of which include hydrolyzed, intact, naturally and/or chemically modified cornstarch, maltodextrin, glucose polymers, sucrose, corn syrup, corn syrup solids, rice or potato derived carbohydrate, glucose, fructose, lactose, high fructose corn syrup and indigestible oligosaccharides such as fructooligosaccharides (FOS), and combinations thereof.

Non-limiting examples of proteins suitable for use in the nutritional compositions include hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof. The proteins for use herein can also include, or be entirely or partially replaced by, free amino acids known for use in nutritional products, non-limiting examples of which include tryptophan, glutamine, tyrosine, methionine, cysteine, arginine, and combinations thereof. Other (non-protein) amino acids typically added to nutritional products include carnitine and taurine. In some cases, the D-forms of the amino acids are considered as nutritionally equivalent to the L-forms, and isomer mixtures are used to lower cost (for example, D,L-methionine).

Non-limiting examples of other lipids suitable for use in the nutritional compositions include coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, linseed oil, flaxseed oil, evening primrose oil, and combinations thereof.

In addition to these food grade oils, structured lipids may be incorporated if desired. Structured lipids are predominantly triacylglycerols containing mixtures of medium and long chain fatty acids on the same glycerol molecule. Structured lipids are described in U.S. Pat. Nos. 6,194,37 and 6,160,007, which descriptions are also incorporated by reference herein.

The nutritional compositions of the present invention may further comprise any of a variety of vitamins in addition to the carotenoids described hereinbefore, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, chromium, carnitine, inositol, salts and derivatives thereof, and combinations thereof.

The nutritional compositions may further comprise any of a variety of minerals, non-limiting examples of which include calcium, phosphorus, magnesium, iron, zinc, manganese, copper, iodine, sodium, potassium, chloride, selenium, and combinations thereof.

The nutritional compositions of the present invention include those embodiments that comprise per 100 kcal of formula one or more of the following: vitamin A (from about 250 to about 750 IU), vitamin D (from about 40 to about 100 IU), vitamin K (greater than about 4 µg), vitamin E (at least about 0.3 IU), vitamin C (at least about 8 mg), thiamine (at least about 8 µg), vitamin B12 (at least about 0.15 µg), niacin (at least about 250 µg), folic acid (at least about 4 µg), pantothenic acid (at least about 300 µg), biotin (at least about 1.5 µg), choline (at least about 7 mg), and inositol (at least about 2 mg).

The nutritional compositions of the present invention include those embodiments that comprise per 100 kcal of formula one or more of the following: calcium (at least about 50 mg), phosphorus (at least about 25 mg), magnesium (at least about 6 mg), iron (at least about 0.15 mg), iodine (at least about 5 µg), zinc (at least about 0.5 mg), copper (at least about 60 µg), manganese (at least about 5 µg), sodium (from about 20 to about 60 mg), potassium (from about 80 to about 200 mg), chloride (from about 55 to about 150 mg), and selenium (at least about 0.5 µg).

The nutritional compositions of the present invention may further comprise other optional components that may modify the physical, chemical, aesthetic or processing characteristics of the compositions or serve as pharmaceutical or additional nutritional components when used in the targeted population. Many such optional ingredients are known or otherwise suitable for use in food and nutritional products, including infant formulas, and may also be used in the nutritional compositions of the present invention, provided that such optional materials are compatible with the essential materials described herein, are safe for their intended use, and do not otherwise unduly impair product performance.

Non-limiting examples of such optional ingredients include preservatives, additional anti-oxidants, emulsifying agents, buffers, colorants, flavors, nucleotides and nucleosides, probiotics, prebiotics, lactoferrin and related derivatives, thickening agents and stabilizers.

For powder embodiments of compositions of the present invention, the above-described methods of use further comprise reconstitution of the powder with a suitable aqueous liquid, preferably water, followed by oral or enteral administration of the resulting nutritional liquid to provide the person with their sole, primary, or supplemental nutrition. Such dilution may be in an amount sufficient to provide a caloric density appropriate for the patient population to which the formula is directed.

The nutritional formulas of the present invention may have any caloric density suitable for the targeted or intended patient population, or provide such a density upon reconstitution of a powder embodiment or upon dilution of a liquid concentrate embodiment. Most common caloric densities for the infant formulas embodiments of the present invention are generally at least about 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in pre-term or low birth weight infants, and the 20-21 kcal/fl oz (675-680 to 700 kcal/liter) formulas are more often used in term infants. Non-infant and adult nutritional compositions may have any caloric density suitable for the targeted or intended population.

For powder embodiments of the present invention, such powders are typically in the form of flowable or substantially flowable particulate compositions, or at least particulate compositions that can be easily scooped and measured with a spoon or similar other device, wherein the compositions can easily be reconstituted by the intended user with a suitable aqueous fluid, typically water, to form a liquid nutritional formula for immediate oral or enteral use. In this context, "immediate" use generally means within about 48 hours, most typically within about 24 hours, preferably right after reconstitution. These powder embodiments include spray dried, agglomerated, dry mixed or other known or otherwise effective particulate form. The quantity of a nutritional powder required to produce a volume suitable for one serving can vary.

The nutritional compositions of the present invention may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

The nutritional compositions of the present invention may be prepared by any known or otherwise effective technique suitable for making and formulating nutritional compositions or similar other compositions, variations of which may depend upon variables such as the selected product form, ingredient combination, packaging and container selection, and so forth, for the desired nutritional formula. Such techniques and variations for any given formula are easily determined and applied by one of ordinary skill in the nutritional formulation or manufacturing arts.

The nutritional compositions of the present invention, including the exemplified formulas described herein, can therefore be prepared by any of a variety of known or otherwise effective formulation or manufacturing methods. These methods most typically involve the initial formation of an aqueous slurry containing the carbohydrates, proteins, lipids, stabilizers or other formulation aids, vitamins, minerals, or combinations thereof. The slurry is emulsified, pasteurized, homogenized, and cooled. Various other solutions, mixtures, or other materials may be added to the resulting emulsion before, during, or after further processing. This emulsion can then be further diluted, heat-treated, and packaged to form a ready-to-feed or concentrated liquid, or it can be heat-treated and subsequently processed and packaged as a reconstitutable powder, e.g., spray dried, dry mixed, or agglomerated. Other suitable methods for making nutritional formulas are described, for example, in U.S. Pat. No. 6,365,218, U.S. Pat. No. 6,589,576, U.S. Pat. No. 6,306,908, U.S. Patent Application 20030118703 A1, the descriptions of which are incorporated herein by reference in their entireties.

As noted, the VLC-PUFAs produced by the methods of the present invention are also suitable for use as therapeutic (pharmaceutic) and experimental agents. An embodiment of the present invention comprises the use of the VLC-PUFAs for treatment of various deficiencies, disorders and conditions in infants and adults as discussed elsewhere herein. Preferred parenteral routes of administration include, but are not limited to, subcutaneous, intradermal, intravenous, intramuscular and intraperitoneal routes. The present invention contemplates compositions of VLC-PUFAs and a carrier suitable for therapeutic delivery. As used, herein, a "carrier" refers to any substance suitable as a vehicle for delivering a molecule or composition to a suitable in vivo site of action. Examples of such carriers include, but are not limited to water, phosphate buffered saline (PBS), Ringer's solution, dextrose solution, serum-containing solutions, Hank's solution and other aqueous physiologically-balanced solutions. Acceptable protocols to administer the present compositions in an effective manner include individual dose size, number of doses, frequency of dose administration, and mode of administration. Determination of such protocols can be accomplished by those skilled in the art depending upon a variety of variables known in the art. Other embodiments of the present invention comprises VLC-PUFA compositions for treatment of adults or non-infants.

Acceptable protocols for administration of the VLC-PUFA compositions include parenteral feeding techniques or encapsulating oil recovered from a host organism of the present invention in a capsule, such as a gelatin (i.e., digestible) capsule, for oral administration and/or in a liquid diet formulation. A liquid diet formulation can comprise a liquid composition containing nutrients suitable for supplementing a diet or nutrients sufficient as a complete diet. For pharmaceutical use (human or veterinary), the VLC-PUFA compositions described herein are preferably administered orally but can be administered by any route by which they may be successfully absorbed, e.g., parenterally (e.g., subcutaneously, intramuscularly or intravenously), rectally or vaginally or topically, for example, as a skin ointment or lotion. The VLC-PUFAs of the present invention may be administered alone or in combination with a pharmaceutically acceptable carrier or excipient. Where available, gelatin capsules are the preferred form of oral administration. Dietary supplementation as set forth above also can provide an oral route of administration. The VLC-PUFAs of the present invention may be administered in conjugated forms, or as salts, esters, triacylglycerols, phospholipids, whole lipids, amides or prodrugs of the fatty acids.

Any pharmaceutically acceptable salt is encompassed by the present invention; especially preferred are the sodium, potassium or lithium salts. The preferred esters are the ethyl esters. As solid salts, the VLC-PUFAs also can be administered in tablet form. For intravenous administration, the VLC-PUFAs may be incorporated into commercial lipid emulsion formulations such as INTRALIPIDS.

The VLC-PUFA compositions contemplated for use in the present invention may be delivered to the human or animal recipient (e.g., dogs, cats, pigs, sheep, goats, chickens, turkeys, zoo animals, other livestock, horses) via oral dosage forms, such as a capsules, powders, tablets, oils, feed stock, or other supplements, as described for example in U.S. Pat. No. 6,641,837 (Col. 3-4), U.S. Pat. No. 6,652,879 (Col. 1-4), U.S. Pat. No. 7,264,824 (Col. 1-3, and WO 90/04391 and WO 96/36329 cited therein), U.S. Pat. No. 7,112,609 (Col. 12-13), U.S. Pat. No. 5,948,818 (Col. 1-8), U.S. Pat. No. 6,726,924 (Col. 1-6), U.S. 2006/0264409 A1 paragraph 64-90, and all U.S. patents cited therein.

The lipid composition of the spermatozoan membrane may be a major determinant of motility, cold sensitivity and a wide selection of factors associated with overall viability within fresh ejaculates or stored ejaculates maintained at −196° C. for artificial insemination. Accordingly, the composition of the present invention may further comprise an antioxidant to enhance sperm function and/or viability. The nutritional and pharmaceutical compositions described herein may be used to improve male and/or female fertility, particularly in mammalian species such as e.g., cattle, pigs, sheep, humans, dogs, cats, goats, horses, and zoo and livestock animals.

In a further aspect, the present invention provides a method of enhancing sperm function and/or viability, comprising adding to the semen of an animal substantially sperm-free seminal fluid containing a VLC-PUFA, and optionally an antioxidant.

The seminal fluid is preferably produced from the semen of another animal which may have been vasectomised or from whose semen sperm have been removed. The mixture of the semen and seminal fluid can then be stored at low temperature for use in artificial insemination. The semen in this aspect of the invention may already have been boosted in function or viability by virtue of the animal having antioxidant and/or other VLC-PUFAs administered to it. The VLC-PUFA is preferably administered to the animal in an amount of, for example, at least 1-10 mg/kg of body weight, more preferably 10-1000 mg/kg.

The invention also provides a method of enhancing the function and/or viability of sperm, the method comprising controlling the VLC-PUFA content of the sperm, preferably the plasma membrane of the sperm, although the control of VLC-PUFA content of the seminal plasma can also be of benefit.

The invention also provides a method of combating sperm dysfunction, comprising controlling the VLC-PUFA content of the sperm, preferably the content of the sperm plasma membrane, e.g., by exposing the sperm to one or more VLC-PUFAs contemplated herein.

The VLC-PUFAs can be added directly to the ejaculate, or can be administered to an animal to enhance the function and/or viability of sperm from that animal. In such a case, the VLC-PUFAs are preferably administered in quantities of at least 0.1 to 1000 mg/kg body weight. The VLC-PUFAs can be provided in substantially pure form (e.g., 95% or more) or in combination with a pharmaceutical carrier or excipient, or in impure form. The VLC-PUFAs may be incorporated into the fatty acid pool of the sperm, or may remain in the seminal fluid in order to exert its beneficial effects. The viability can be further enhanced by increased mobility, cold resistance or related factors. It has been shown that mice deficient in VLC-PUFA are sterile and possess a lack of mature sperm cells, which is a frequent cause of male infertility in humans[31]. Increasing the content therein of VLC-PUFAs (C28-C38) (which are normally present in sperm cells), will lead to the production of viable, mature sperm cells resulting in restored fertility.

The present invention further comprises in one embodiment a method of treating subjects that have Stargardt disease, retinal diseases, and macular degeneration (or treating subjects to prevent macular degeneration) by dietary supplementation with C28-C38 n-3 fatty acids, and/or C28-C38 n-6 fatty acids, for protecting or slowing down photoreceptor degeneration in these patients.

Stargardt-like macular dystrophies are a group of progressive photoreceptor degenerative disorders that eventually lead to loss of vision. They are distinct from other types of macular degeneration because their phenotype is evident in the early years, even in the first decade, as opposed to age-related macular degeneration (AMD), which is the most common cause of blindness in people over 60 years of age. Three mutations in the Elovl4 gene are known to cause one form of the disease named Stargardt-3 (STGD3). However, the fact that ELOVL4 is indeed necessary for fatty acid elongations and the specific step(s) in the elongation process it catalyzes was not demonstrated prior to the present work.

In another embodiment, the VLC-PUFA compositions described elsewhere herein may be used as a biofuel. Biofuels are renewable resources produced by living organisms. Biofuels such as biodiesel are typically fatty acid alkyl esters derived from the transesterification of oils generated from plants, algae, bacteria and fungi. VLC-PUFA (such as the C28-C38 PUFAs described in this patent application) are a potential source of biofuel. They can be produced by the expression of ELOVL4 in plant material, bacteria, algae, yeast, etc., as described elsewhere herein resulting in the generation of these fatty acids, which can be two to three times as long as those fatty acids typically used for biodiesel and thus provide more energy per molecule. These fatty acids can then be extracted and processed into biofuels such as biodiesel.

EXPERIMENTAL

Figure 2:
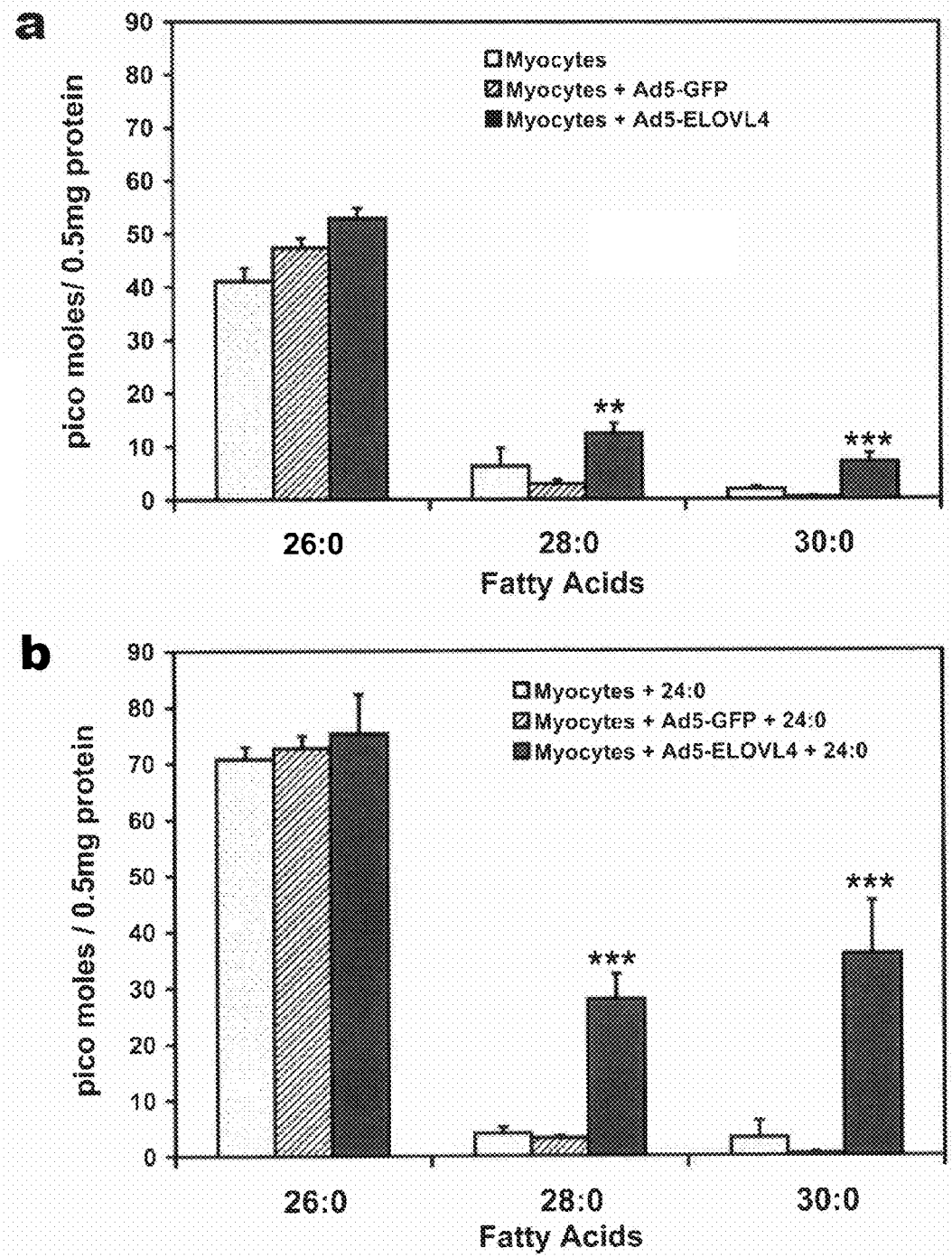
FIG. 2: Synthesis of 28:0 and 30:0 fatty acids from 24:0 fatty acid supplementation is enhanced in myocytes expressing mouse Elovl4 transgene. Two controls (GFP expressing and non-transduced myocytes) and mouse ELOVL4 expressing myocytes were treated without (a) or with (b) 24:0 for 72 h. While there were no significant differences between the levels of 28:0 and 30:0 between the control groups, there were significant differences in levels of 28:0 and 30:0 in mouse ELOVL4 expressing myocytes compared to the two controls.  $p<0.01$, * $p<0.001$, (n=3).
Figure 3:
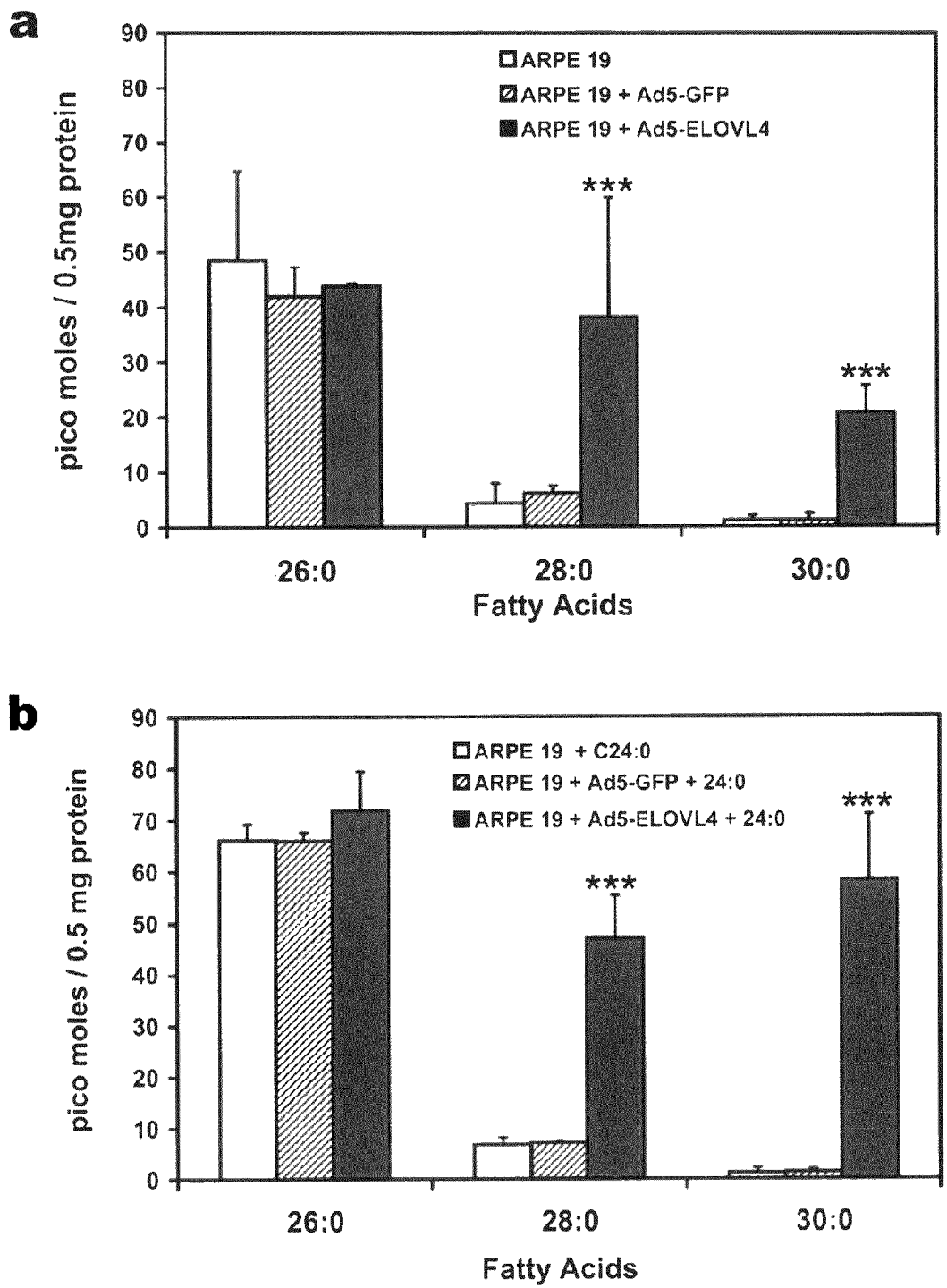
FIG. 3: Elongation of very long chain fatty acids is enhanced in ARPE-19 cells expressing mouse ELOVL4. ARPE-19 cells non-transduced, Ad5-GFP or Ad5-mELOVL4 transduced were treated without 24:0 fatty acids (a) or with 24:0 fatty acids (b) for 48 h. There were no significant differences in levels of 28:0 and 30:0 fatty acids in the normal ARPE-19 or GFP expressing cells with or without 24:0. ELOVL4 expression in the cells resulted in 7.5 fold increase in 28:0 with or without 24:0. 30:0 fatty acid was increased 20 fold in ELOVL4 expressing cells and upon treatment with 24:0 (b) there was a 50 fold increase in the amount of 30:0 made compared to the two controls. *** $p<0.001$, (n=3).

We investigated the role of the Elovl4 gene and the protein encoded in the biosynthesis of very long chain fatty acids (VLCFAs) in rat neonatal cardiac myocytes (FIG. 2) and a human retina epithelium cell line (ARPE-19) (FIG. 3), neither of which express ELOVL4 mRNA or protein to any extent (FIG. 1a). We have demonstrated herein that elongation of fatty acid C26 to fatty acids C28-C38 is enhanced in cells expressing ELOVL4. Adenovirus-mediated expression of ELOVL4 protein in myocytes or ARPE-19 cells resulted in elongation of the precursor tetracosanoic acid/lignoceric acid (24:0) to hexacosanoic acid (26:0) among all treatment groups. However, ELOVL4-expressing cells further elongated 26:0 to octacosanoic acid/montanic acid (28:0) and triacontanoic acid/mellisic acid (30:0) at significantly higher levels than control cells. Likewise, only ELOVL4-expressing cells elongated the polyunsaturated fatty acids eicosapentaenoic acid (20:5n3) (FIG. 4b) and docosapentaenoic acid (22:5n3) (FIG. 4c) to C28-C38 polyunsaturated fatty acids (PUFA). We provide direct evidence, for the first time, for the specific step in fatty acid metabolism catalyzed by ELOVL4. The present work demonstrates that these steps are important in the synthesis of VLC-FA and VLC-PUFA (C28-C38) that are esterified into phosphatidylcholine, sphingomyelin, ceramides and free fatty acids in retina, brain, skin, testis and sperm.

To establish the specific step that the ELOVL4 protein catalyzes in VLCFA elongation, we over-expressed transgenic mouse ELOVL4 protein in rat neonatal cardiomyocytes and in a human retinal pigment epithelium cell line (ARPE-19). These cells have none or low detectable levels of endogenous ELOVL4 protein and mRNA (FIG. 1a). The endogenous expression of ELOVL4 in rat cardiomyocytes cells was ~2500-fold less than that found in the retina by quantitative real-time PCR (FIG. 1). The highest level of ELOVL4 expression was detected in rat retina, followed by skin; brain and testis also showed significant expression which was ~1000 times lower than the level found in retina; heart and liver showed negligible levels of expression, corresponding well with previous observations in mice[19]. Minimal ELOVL4 expression was observed in ARPE19 cells (FIG. 1a). When the cardiomyocytes and ARPE19 cells were transduced with adenovirus carrying mouse ELOVL4 (Ad5-mELOVL4) and subjected to qRT-PCR, ELOVL4 expression was increased 1000- and 3000-fold, respectively, compared to non-transduced cells. This expression level is comparable to that observed in rat retina (FIG. 1a).

Figure 1B:
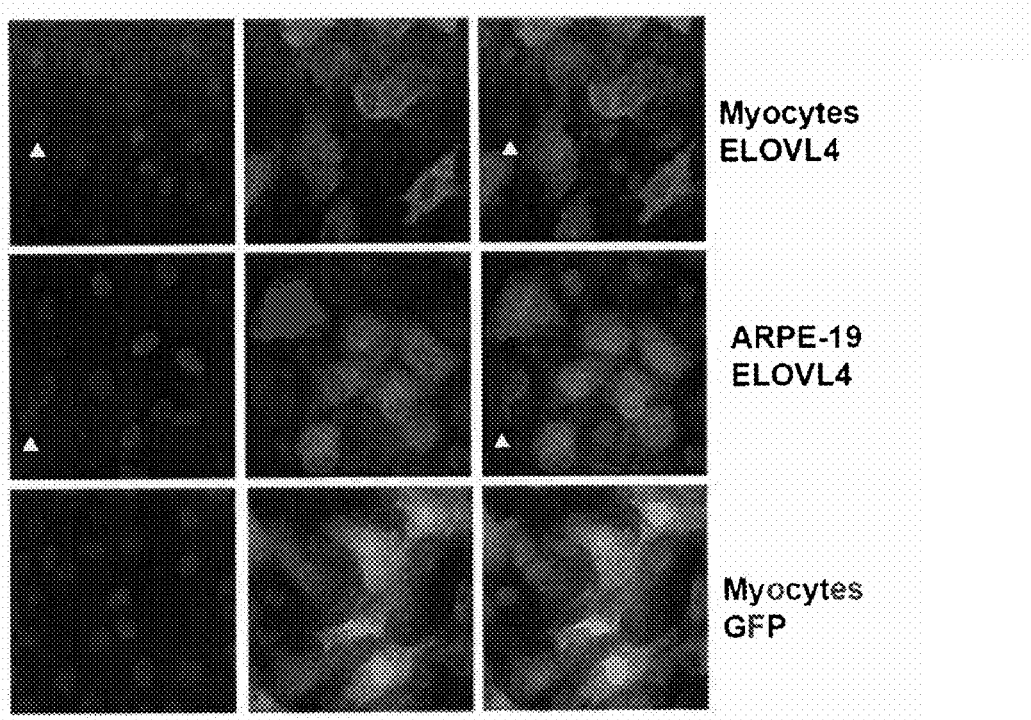
Figure 1C:
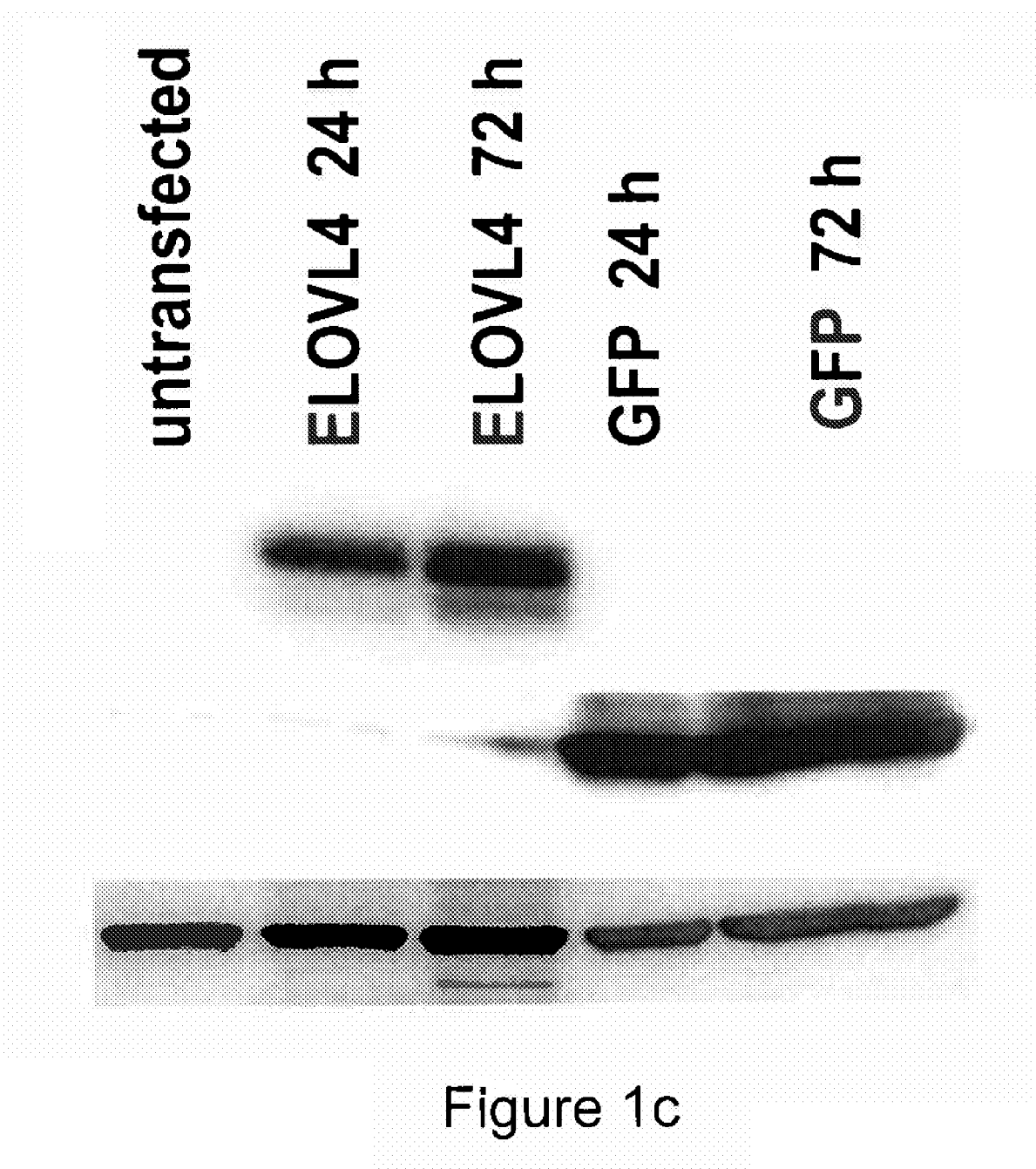

Further, adenoviral delivery and expression of ELOVL4 or GFP proteins in transduced cells was confirmed by immunocytochemical labeling for ELOVL4 and GFP (FIG. 1b). Non-transduced cells did not show any expression of ELOVL4 in both cell types (FIG. 1b, arrows). Finally, protein expression levels in the transduced cells were confirmed by Western blot (FIG. 1c). Mouse ELOVL4 protein was not detected in control cells (non-transduced and Ad5-GFP transduced cells), respectively, but was highly abundant in cardiomyocytes (FIG. 1c) and ARPE-19 cells transduced with Ad5-mELOVL4 (data not shown).

We then tested whether expression of mouse ELOVL4 can lead to elongation of a saturated long chain fatty acid substrate, lignoceric acid (24:0), a precursor of VLCFAs greater than 26 carbons. From the fatty acid data obtained by GC/MS, it was found that the cells, irrespective of ELOVL4 overexpression, were able to internalize the precursors and elongate them to C26 products (FIG. 2a&b). These elongation steps are possibly catalyzed by other elongases as indicated in previous studies[9,10]. The fatty acid profiles were, however, remarkably different between the controls (non-transduced and Ad5-GFP transduced) and the Ad5-mELOVL4 transduced cells in terms of elongation past C26. Even in the absence of exogenous 24:0 precursors, the Ad5-mELOVL4-transduced cells showed three-fold increases in the levels of 28:0 and 30:0 compared to controls (FIG. 2a). Upon treatment with 24:0, cardiomyocytes transduced with Ad5-GFP and non-transduced controls had no change in their fatty acid profiles. However, the Ad5-mELOVL4 transduced cells showed significant elongation of the 26:0 fatty acids to 28:0 fatty acids (79.1% increase compared to 11.3% and 9.3% in myocytes and GFP expressing cells, respectively). The 28:0 fatty acid was further elongated to 30:0 (FIG. 2b). Compared to the non-transduced and Ad5-GFP-transduced cells, which showed no differences in the levels of 28:0 and 30:0 fatty acids, the Ad5-mELOVL4-transduced cells showed statistically significant increases in 28:0 and 30:0 even without addition of the 24:0 precursor as determined by Multivariate ANOVA with post-hoc Scheffe test (p<0.01, n=3). Similar results were obtained from ARPE-19 cells transduced with Ad5-mELOVL4 and supplemented with or without 24:0 fatty acid (FIG. 3a&b). Expression of ELOVL4 in the ARPE-19 cells resulted in ~20- and 50-fold increases in 28:0 and 30:0 fatty acid, respectively, compared to controls.

These results have shown by the "gain of function" approach that, indeed, ELOVL4 protein is involved in elongation of saturated VLCFAs that are normally incorporated into sphingolipids and ceramides that are necessary for skin barrier permeability. This supports earlier findings in which ELOVL4 knockout results in neonatal lethality due to defects in skin barrier permeability in ELOVL4 knockout mice, while the heterozygote animals show reduction in levels of very long chain saturated fatty acids, ceramides and sphingolipids[12-14]. From these findings we concluded that in the skin, ELOVL4 is responsible for synthesis of very long chain saturated fatty acids that are incorporated into ceramides and sphingolipids to protect the skin from dehydration.

In the retina, however, very long chain saturated fatty acids, sphingolipids and ceramides form a very minor component of the lipid pool[20]. Instead, n-3/n-6 VLC-PUFA (C26-C38) are much more abundant and have been shown to be associated with rhodopsin, the major phototransduction protein in the retina[21,22]. They can be synthesized from long chain polyunsaturated precursors when injected into the vitreal fluid. However, the elongase(s) responsible for their biosynthesis has never been shown[23]. Based on the present data provided herein, we now assert the novel result that the ELOVL4 protein is an enzyme or a co-enzyme that plays a crucial role in biosynthesis of VLC-PUFAs found in the retina, brain, testis and sperm (tissues that express the ELOVL4).

Figure 4A:
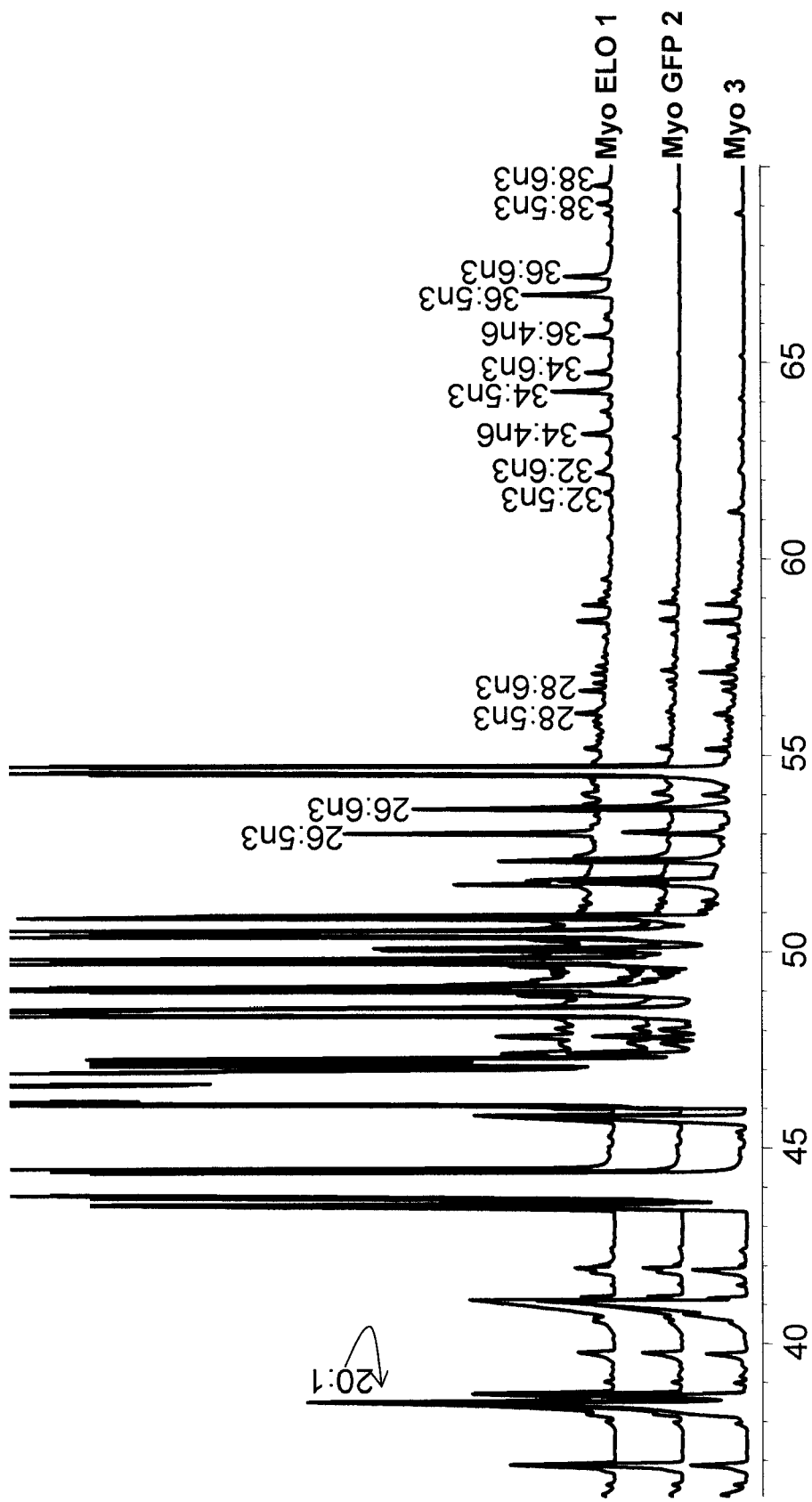
FIG. 4: GC/MS chromatograms illustrating VLC-PUFAs synthesized from 20:5n3 and 22:5n3 fatty acid supplementation in ELOVL4 transduced cells. (a) Cardiomyocytes transduced with mouse ELOVL4 ("Myo ELO1"), GFP transduced cells ("Myo GFP2") and non-transduced cells ("Myo 3") cultured without precursors for 72 h. Presence of ELOVL4 in absence of precursor resulted in elongation of endogenous precursor to generate VLC-PUFAs. Abundances were compared by normalizing chromatograms using the peak height of 20:1 (a fatty acid confirmed to be unaffected by the experimental process). (b) Incubation of the cells with 20:5n3 (EPA) resulted in significant biosynthesis of C28-C38 n-3 VLC-PUFAs in ELOVL4 ("ELO+EPA 30A") transduced cells but not in GFP ("GFP+EPA 30A") and non-transduced cells ("EPA 30A"). (c) Addition of 22:5n3 (DPA) also resulted in the synthesis of n-3 VLC-PUFAs, showing no observable differences from those synthesized in the presence of 20:5n3.
Figure 4B:
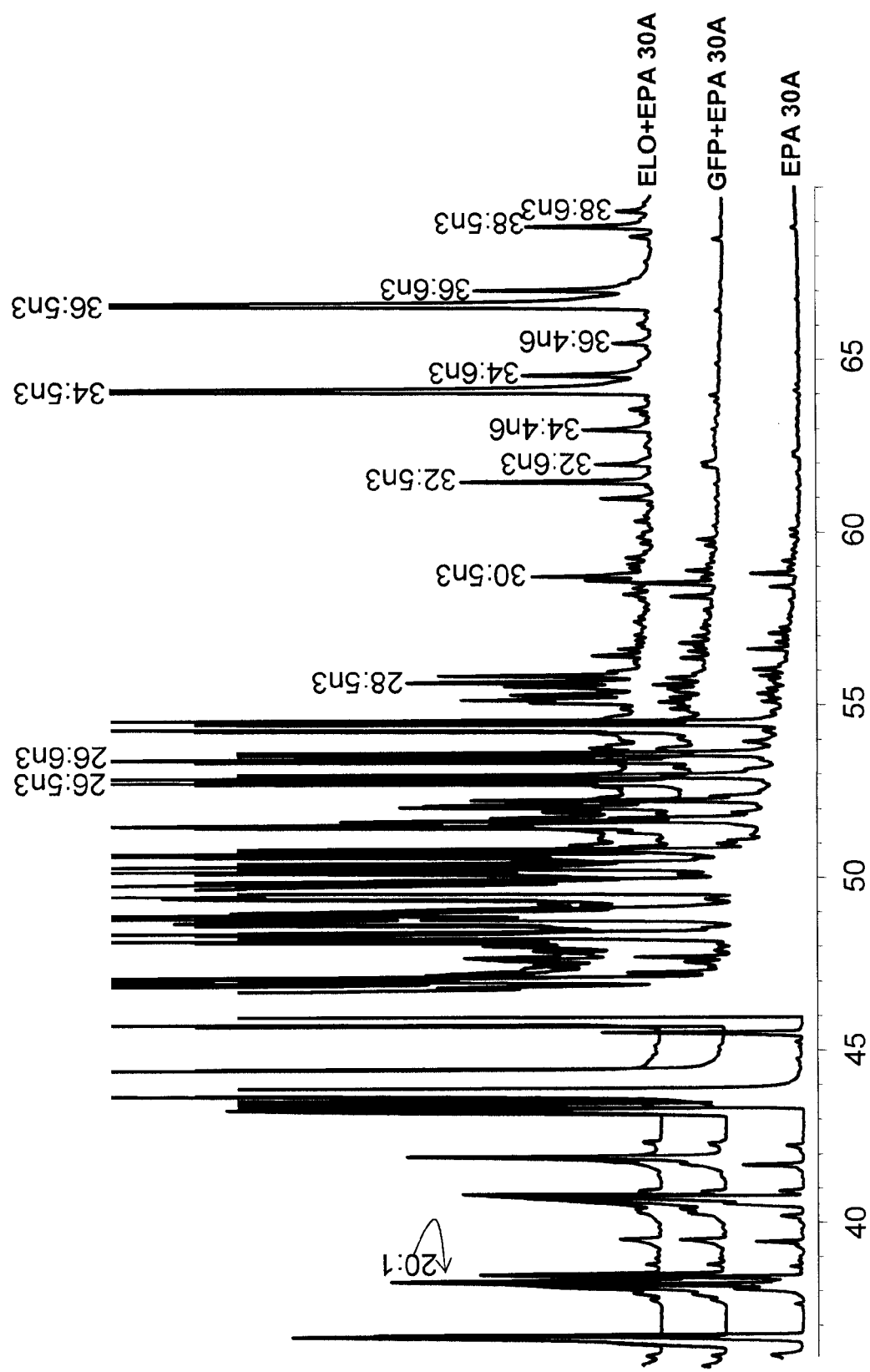
Figure 4C:
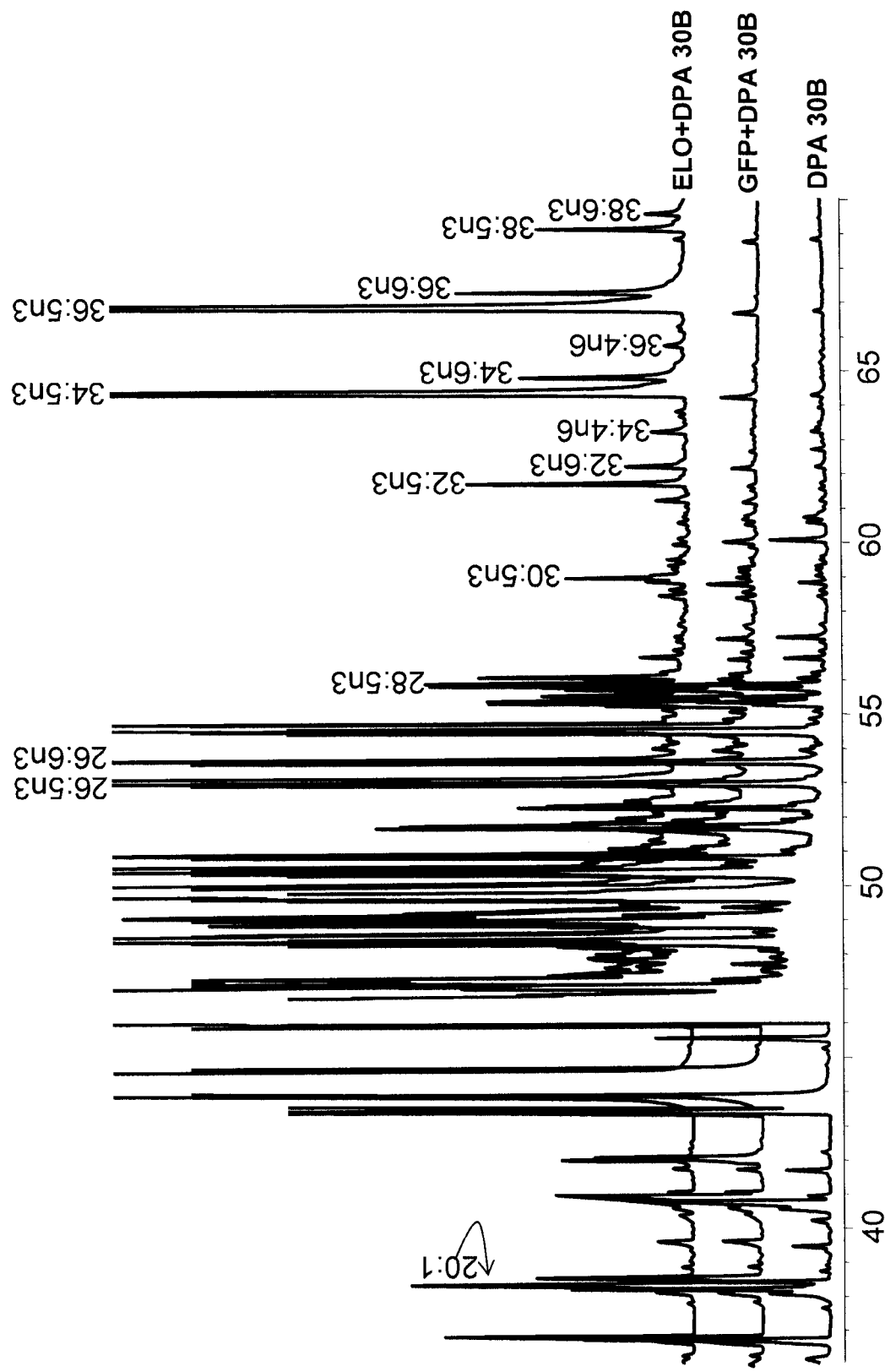

To confirm that ELOVL4 protein actually plays a role in biosynthesis of VLC-PUFAs (>C26), we examined the ability of ELOVL4-transduced cells to elongate the VLC-PUFA precursors eicosapentaenoic acid (EPA; 20:5n3) and docosapentaenoic acid (DPA; 22:5n3). Cardiomyocytes transduced with ELOVL4 or GFP were treated for 72 h with 30 or 40 ug/mL of 20:5n3 or 22:5n3 fatty acid precursors. The results showed that all treatment groups elongated the precursors to C24-C26 n-3 fatty acids without any appreciable differences in their peak areas (FIG. 4a). However, ELOVL4-transduced cells also showed distinct peak sizes of the elongation products 28:5n3, 30:5n3, 32:5n3, 34:5n3, 36:5n3 and 38:5n3 fatty acids from either 20:5n3 or 22:5n3 precursor (FIG. 4b&c). The control cells did not demonstrate these elongation steps (FIG. 4a). In the ELOVL4-transduced cells, the major VLC-PUFA products were 34:5n3 and 36:5n3 fatty acids. In addition, there were some 34:6n3 and 36:6n3 fatty acid products which are probably products from desaturase activities. These findings support observations that Stargardt disease-3 mutation in the mouse Elovl4 gene causes a reduction in the levels of C32-C36 acyl phosphatidylcholines[18]. Thus, Elovl4 is shown herein to be the gene responsible for biosynthesis of very long chain polyunsaturated fatty acids (beyond C26) that are incorporated into ceramides and sphingolipids and very long chain polyunsaturated fatty acid-containing phosphatidylcholines found in the retina, brain and testis, an activity which had not been established[13-15,17,24] prior to the present disclosure.

Previous studies have also shown that the ELO families of proteins are enzymes involved in fatty acid elongation[11,14,15]. Other mammalian ELOVLs that share similar homologies and specific conserved motifs such as dilysine for the endoplasmic reticulum (ER) retention motif (KXKXX) (SEQ ID NO:19), and a conserved histidine-rich motif (HXXHH) (SEQ ID NO:20) believed to act as an iron-chelating ligand used for electron transfer for $O_2$-dependent redox reactions,[3,24] are involved in fatty acid biosynthesis. The present results establish for the first time ELOVL4 as a component of an elongation system that elongates both saturated and polyunsaturated fatty acids.

The results provided herein for cells that do not normally express ELOVL4 mRNA or protein show that ELOVL4 is necessary for the elongation to VLC-FA and VLC-PUFA. The alternative explanations provided above for the results obtained in mutated animals do not apply here, since there is no reason to suspect that the absence of ELOVL4 expression in normal cells functions to suppress an important biological activity in these cells. Without wishing to be bound by theory, a more logical explanation is that the myocytes and ARPE-19 cells have no biological need for the products of ELOVL4, and that the elongation products we observed in both cell types transduced with ELOVL4 are the result of the direct participation of the ELOVL4 protein acting at some step in their elongation. Again, without wishing to be bound by theory, given the known roles of other ELOVL proteins as condensing enzymes, we assert herein that ELOVL4 catalyzes the addition of malonyl-CoA to C26 saturated and PUFA to form C28 compounds, using existing dehydrases and reductases shown to be involved in synthesis of fatty acids of all chain lengths and degrees of unsaturation. We further assert that ELOVL4 catalyzes condensation reactions in the formation of longer chain saturated and PUFA to generate the C30-C38 fatty acids we characterized in our GC/MS analyses.

Methods

Construction of Recombinant Adenoviruses Carrying Mouse Elovl4

Recombinant adenovirus carrying the mouse Elovl4 gene (Ad5-mELOVL4) was constructed following Clontech's Adeno X Expression systems 2 with creator technology protocols (Clontech, Palo Alto, Calif.) and supplementary methods online. Recombinants were selected, sequenced, confirmed, purified, and digested with Pac I and then transfected into human embryonic kidney 293 cells (HEK-293) to generate virus particles. The recombinant viruses were prepared as high-titer stocks through the propagation in 293 cells by double cesium chloride purification, dialyzed against a 10 mM Tris (pH 8.0) buffer that contained 80 mM NaCl, 2 mM $MgCl_2$ and 10% glycerol[25]. Infectious adenovirus titer was determined in triplicate by plaque forming assay and expressed as plaque-forming units (pfu) per ml.

Cell Cultures with Ad5-Mouse-ELOVL4

Rat neonatal cardiomyocytes were isolated from 1- or 2-day-old rats using the National Cardiomyocyte Isolation System (Worthington, Lakewood, N.J.). The isolated cells ($5 \times 10^6$ cells) were plated in 10-cm tissue culture plates and cultured in DMEM/F-12 (1:1) medium containing 10% (v/v) FBS and 5% (v/v) horse serum supplemented with 1 mM sodium pyruvate, penicillin (100 U/ml) and streptomycin (100 U/ml), at 37° C. in a tissue culture incubator with constant supply of 5% $CO_2$ in 95% relative humidity. Cells were used for experiments after two to three days in culture. ARPE-19 cells ($2 \times 10^6$) were cultured under the same conditions as myocytes.

Adenovirus infections of myocytes and ARPE-19 cells were carried out as described[17,26]. After 24 h incubation, the infection medium was replaced with normal [15% (vol/vol) serum] culture medium supplemented separately with 50 or 100 µg/ml of the sodium salt of lignoceric acid (24:0) or 30 or 40 ug/ml of 20:5n3 or 22:5n3, which had been conjugated to bovine serum albumin fraction V[27]. After incubation in lipid precursors for 48 or 72 h, cells were washed in phosphate buffered saline (PBS) containing 50 µM fatty acid free bovine serum albumin fraction V, then twice more with only PBS, scraped and stored as pellets at −80° C. until used.

RNA Isolation and cDNA Synthesis

RNA was isolated and purified from all the collected rat tissues, cultured cardiomyocytes, and ARPE-19 cells using "PureLink™ Micro-to-Midi Total RNA Purification System" from Invitrogen by following the manufacturer's protocol.

Production of Affinity-Purified ELOVL4 Antibodies

A synthetic 12-amino acid peptide corresponding to amino acids 301-312 of the mouse ELOVL4 protein was conjugated to keyhole limper hemocyanin and injected subcutaneously into rabbits for polyclonal antibodies production after collection of preimmune serum. Affinity purified antibodies were collected using immobilized peptide antigen (Bethyl Laboratory Inc, Montgomery, Tex.).

Immunofluorescence Labeling of Myocytes and ARPE-19 Cells

Rat neonatal cardiomyocytes were sub-cultured onto poly-L-lysine coated four-well chamber glass slides. Twenty-four hours later, cells were transduced with Ad5-GFP or Ad5-mELOVL4, grown at 37° C. for 24 h, washed twice with ice cold PBS, and fixed at −20° C. in methanol:acetone (1:1, v/v) for 10 min. Ad5-GFP transduced cells were mounted with Vectashield mounting media (Vector laboratories, Inc., Burlingame, Calif.) for microscopy. Ad5-mELOVL4 transduced cells were blocked and permeabilized for 1 h at room temperature in PBS containing 10% (v/v) normal goat serum and 0.1% (v/v) Triton X-100, and treated with anti-ELOVL4 antibody (1:200) overnight at 4° C. Immunofluorescent labeling was visualized using a Zeiss Axioplan 2 fluorescence microscope.

Lipid Extraction and Fatty Acid Derivatization:

Total cellular lipids were extracted as described[30]. To the purified lipid extracts, a mixture of pentadecanoic acid (15:0), heptadecanoic acid (17:0), heneicosanoic acid (21:0), pentacosanoic acid (25:0) and heptacosanoic acid (27:0) was added for use as internal standards. 1.0 mL of 16.6% concentrated HCl in methanol was added and the tubes were sealed under $N_2$ with Teflon lined caps and heated at 75° C. for 5 hours. The tubes were cooled on ice and fatty acid methyl esters were extracted three times with 2.0 mL hexane. The hexane layers were dried under $N_2$, dissolved in 50 µL of hexane, sonicated, spotted on thin layer chromatography (TLC) plates, and developed in hexane:ether (80:20). The plates were stained with dichlorofluorescein; fatty acid methyl ester bands were then scraped from the TLC plates and collected. 2.0 mL of absolute ethanol were added to the scraped bands and the mixture was capped under $N_2$ and sonicated for 10 minutes. Fatty acid methyl esters were extracted three times with 2.4 mL hexane after adding 2.0 mL of de-ionized water. The combined hexane layers were dried under $N_2$ and dissolved in 20 µL nonane for GC-MS analysis.

FAME Analysis by GC-MS

Fatty Acid Methyl Esters (FAMEs) were identified and quantified using an Agilent Technologies 6890N gas chromatograph (GC) with a 5975B inert XL mass spectrometer (MS) detector (Agilent Technologies, Wilmington, Del.). The GC-MS was operated in the electron impact (EI) single ion monitoring (SIM) mode. For saturated FAME analysis, the injection volume was 1 µl and the inlet, held at 320° C., was set to pulsed splitless mode. An Agilent Technologies HP-5 ms column (30 m×0.25 mm×0.25u) was used with a helium carrier gas flow rate of 1.2 ml/min. The oven temperature began at 160° C., was ramped to 320° C. at 3° C./min, and held at 320° C. for 20 minutes. The MS transfer line, ion source and quadrupole temperatures were 320° C., 230° C., and 150° C., respectively. The 26:0, 28:0 and 30:0 response values were obtained using the m/z ratios 410.4, 438.4, and 466.5, respectively. Sample concentrations were determined by comparison to external standards, using 25:0 and 27:0 as internal standards. Multivariant ANOVA with post-hoc Scheffe tests determined statistical significance ($p<0.05$).

For very long polyunsaturated FAME analysis, the injection volume was 1 μl and the inlet, held at 290° C., was set to pulsed splitless mode. An SGE BPX70 column (35 m×0.22 mm×0.25u) was used with a helium carrier gas flow rate of 1.2 ml/min (SGE, Austin, Tex.). The oven temperature began at 90° C. for 10 minutes, was ramped to 290° C. at 3° C./min, and held at 290° C. for 12.3 minutes. The MS transfer line, ion source and quadrupole temperatures were 290° C., 230° C., and 150° C., respectively. The PUFA response values were obtained using the nm/z ratios 79.1, 108.1, and 150.1 in SIM mode. Abundances were compared by normalizing peak areas to nanomoles of 20:1, using 23:0 as an internal standard.

As used herein, "effective amount" means an amount of a VLC-PUFA component of the composition that is nontoxic but sufficient to provide the desired effect and performance at a reasonable benefit/risk ratio attending any dietary supplement or therapeutic composition.

Where used herein, the singular forms "a," "an," and "the" are understood to refer to the plural forms of the subject, unless the context clearly dictates otherwise.

The compositions and corresponding methods of the present invention can comprise, consist of, or consist essentially of, the essential elements and limitations of the invention described herein, as well as any additional or optional ingredients, components, or limitations described herein or otherwise useful in compositions having nutritional and therapeutic applications as described herein.

ABBREVIATIONS

Ad5, Adenovirus type 5; Ad5-mELOVL4, Ad carrying mouse Elovl4 gene; GFP, green fluorescent protein; Ad5-GFP, Ad5 carrying GFP gene; VLCFA, very long chain saturated fatty acid; VLC-PUFA, very long chain polyunsaturated fatty acid; ELOVL4, Elongation of Very Long Chain Fatty Acids-4; 24:0, lignoceric acid (tetracosanoic acid); 26:0, hexacosanoic acid; 28:0, octacosanoic acid/montanic acid; 30:0, triacontanoic acid/mellisic acid.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, items of manufacture, compositions of matter, means, methods and steps described in the specification. As one of ordinary skill in the art will readily appreciate from the disclosure of the present invention, processes, items of manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, items of manufacture, compositions of matter, means, methods, or steps.

Each of the patents, published patent applications, or references listed or described herein is expressly incorporated by reference herein in its entirety.

CITED REFERENCES

[1] K. Zhang, M. Kniazeva, M. Han et al., *Nature genetics* 27 (1), 89 (2001).

[2] A. Maugeri, F. Meire, C. B. Hoyng et al., *Investigative opthalmology & visual science* 45 (12), 4263 (2004); A. O. Edwards, L. A. Donoso, and R. Ritter, 3rd, *Investigative opthalmology & visual science* 42 (11), 2652 (2001); T. R. Vrabec, A. Tantri, A. Edwards et al., *American journal of opthalmology* 136 (3), 542 (2003).

[3] C. Grayson and R. S. Molday, *The Journal of biological chemistry* 280 (37), 32521 (2005).

[4] R. Ambasudhan, X. Wang, M. M. Jablonski et al., *Genomics* 83 (4), 615 (2004).

[5] V. Vasireddy, C. Vijayasarathy, J. Huang et al., *Molecular vision* 11, 665 (2005).

[6] S. Umeda, R. Ayyagari, M. T. Suzuki et al., *Experimental animals/Japanese Association for Laboratory Animal Science* 52 (2), 129 (2003).

[7] P. Tvrdik, R. Westerberg, S. Silve et al., *The Journal of cell biology* 149 (3), 707 (2000).

[8] C. S. Oh, D. A. Toke, S. Mandala et al., *The Journal of biological chemistry* 272 (28), 17376 (1997).

[9] A. Jakobsson, R. Westerberg, and A. Jacobsson, *Progress in lipid research* 45 (3), 237 (2006).

[10] R. Westerberg, J. E. Mansson, V. Golozoubova et al., *The Journal of biological chemistry* 281 (8), 4958 (2006); R. Westerberg, P. Tvrdik, A. B. Unden et al., *The Journal of biological chemistry* 279 (7), 5621 (2004).

[11] A. E. Leonard, S. L. Pereira, H. Sprecher et al., *Progress in lipid research* 43 (1), 36 (2004); Y. Ge, Z. Chen, Z. B. Kang et al., *Anticancer research* 22 (2A), 537 (2002).

[12] W. Li, R. Sandhoff, M. Kono et al., *International journal of biological sciences* 3 (2), 120 (2007).

[13] A. McMahon, I. A. Butovich, N. L. Mata et al., *Molecular vision* 13, 258 (2007).

[14] V. Vasireddy, Y. Uchida, N. Salem, Jr. et al., *Human molecular genetics* 16 (5), 471 (2007).

[15] D. J. Cameron, Z. Tong, Z. Yang et al., *International journal of biological sciences* 3 (2), 111 (2007).

[16] G. Karan, C. Lillo, Z. Yang et al., *Proceedings of the National Academy of Sciences of the United States of America* 102 (11), 4164 (2005).

[17] W. Li, Y. Chen, D. J. Cameron et al., *Vision research* 47 (5), 714 (2007).

[18] A. McMahon, S. N. Jackson, A. S. Woods et al., *FEBS letters* (2007).

[19] M. N. Mandal, R. Ambasudhan, P. W. Wong et al., *Genomics* 83 (4), 626 (2004).

[20] S. J. Fliesler and R. E. Anderson, *Progress in lipid research* 22 (2), 79 (1983).

[21] M. I. Aveldano, *Biochemistry* 27 (4), 1229 (1988).

[22] M. I. Aveldano and H. Sprecher, *The Journal of biological chemistry* 262 (3), 1180 (1987).

[23] M. Suh and M. T. Clandinin, *Current eye research* 30 (11), 959 (2005).

[24] T. Chertemps, L. Duportets, C. Labeur et al., *Proceedings of the National Academy of Sciences of the United States of America* 104 (11), 4273 (2007).

[25] V. Denic and J. S. Weissman, *Cell* 130 (4), 663 (2007).

[26] J. Xiao and J. Chodosh, *Investigative opthalmology & visual science* 46 (10), 3777 (2005).

[27] Z. B. Kang, Y. Ge, Z. Chen et al., *Proceedings of the National Academy of Sciences of the United States of America* 98 (7), 4050 (2001); Y. Ge, X. Wang, Z. Chen et al., *Journal of neurochemistry* 82 (6), 1360 (2002).

[28] J. M. Street, D. W. Johnson, H. Singh et al., *The Biochemical journal* 260 (3), 647 (1989).

[29] D. Raz-Prag, R. Ayyagari, R. N. Fariss et al., *Investigative opthalmology & visual science* 47 (8), 3603 (2006); V.

Vasireddy, M. M. Jablonski, M. N. Mandal et al., *Investigative opthalmology & visual science* 47 (10), 4558 (2006).

[30] R. E. Martin, M. H. Elliott, R. S. Brush et al., *Investigative opthalmology & visual science* 46 (4), 1147 (2005).

[31] Stoffel, W., Holz, B., Jenke, B., Binczek, E., Gunter, R. H., Kiss, C., Karakesisoglou, I., Thevis, M., Weber, A-A., Arnhold, S., and Addicks, K. Delta-6-Desaturase (FADS2) deficiency unveils the role of w3 and w6-polyunsaturated fatty acids. The EMBO Journal 2008 (27):2281-2292.

[32] Agostoni, C. Role of long-chain polyunsaturated fatty acids in the first year of life. J Pediatr Gastroenterol Nutr. 2008 November; 47 Suppl 2:S41-4.

---

What is claimed is:

1. A method of producing at least one very long chain polyunsaturated fatty acid (VLC-PUFA) having a chain length of at least 28 carbons, comprising:
   providing a recombinant cell which comprises at least one Elovl4 nucleic acid expression system which encodes an ELOVL4 protein which has ELOVL4 elongase activity;
   culturing the recombinant cell under conditions effective in causing expression of the ELOVL4 protein wherein the ELOVL4 protein causes elongation of an unsaturated fatty acid precursor molecule having 18-26 carbon atoms to form at least one VLC-PUFA having a chain length of at least 28 carbons in the recombinant cell; and
   harvesting the at least one VLC-PUFA from the cultured recombinant cell.

2. The method of claim 1 wherein the Elovl4 expression system which encodes the ELOVL4 protein comprises a nucleic acid which hybridizes to at least one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO: 17 under conditions of medium or high stringency.

3. The method of claim 1 wherein the Elovl4 expression system which encodes the ELOVL4 protein comprises an expression control sequence.

4. The method of claim 1 wherein the ELOVL4 protein is at least 95% identical to at least one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

5. The method of claim 1 wherein the recombinant cell is present in an organism selected from the group consisting of bacteria, fungi, algae, protozoa, plants, and non-human milk-producing animals.

6. The method of claim 1 further comprising purifying the at least one VLC-PUFA harvested from the cultured recombinant cell.

7. The method of claim 1 wherein the recombinant cell produces a plurality of different VLC-PUFAs having chain lengths comprising 28 carbons, 30 carbons, 32 carbons, 34 carbons, 36 carbons, 38 carbons, and/or 40 carbons.

8. The method of claim 1 wherein the at least one VLC-PUFA produced by the recombinant cell is a n3 polyunsaturated fatty acid.

9. The method of claim 8 wherein the n3 polyunsaturated fatty acid is selected from the group consisting of 3n3, 4n3, 5n3, 6n3, 7n3 and 8n3 fatty acids.

10. The method of claim 1 wherein the at least one VLC-PUFA produced by the recombinant cell is a n6 polyunsaturated fatty acid.

11. The method of claim 10 wherein the n6 polyunsaturated fatty acid is selected from the group consisting of 3n6, 4n6, 5n6, 6n6, and 7n6 fatty acids.

12. The method of claim 1 wherein in the step of culturing the recombinant cell the unsaturated fatty acid precursor is provided exogenously.

13. The method of claim 1 wherein the recombinant cell produces a VLC-PUFA profile that differs from an isolated cell which does not comprise the Elovl4 expression system.

14. The method of claim 1 wherein the recombinant cell is present in a genetically-modified non-human milk-producing animal.

15. The method of claim 1 wherein the recombinant cell is present in a non-human mammal or a plant.

16. The method of claim 1 wherein the recombinant cell is a bacterium, fungus, protozoan, or algae.

17. The method of claim 1 wherein at least 5% by weight of the total fatty acids produced by the recombinant cell comprise VLC-PUFAs having chain lengths of at least 28 carbons.

18. A method of producing at least one very long chain polyunsaturated fatty acid (VLC-PUFA) having a chain length of at least 28 carbons, comprising:
providing a recombinant cell which comprises at least one Elovl4 nucleic acid expression system which encodes an ELOVL4 protein which has ELOVL4 elongase activity;
culturing the recombinant cell under conditions effective in causing expression of the ELOVL4 protein wherein the ELOVL4 protein causes elongation of a n3 unsaturated fatty acid precursor molecule having 18-26 carbon atoms to form at least one n3 VLC-PUFA having a chain length of at least 28 carbons in the recombinant cell; and
harvesting the at least one VLC-PUFA from the cultured recombinant cell.

19. The method of claim 18 wherein the chain length of the at least one n3 VLC-PUFA is selected from the group consisting of 28, 30, 32, 34, 36, 38, and 40 carbons.

20. The method of claim 18 wherein the Elovl4 expression system which encodes the ELOVL4 protein comprises a nucleic acid which hybridizes to at least one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO: 17 under conditions of medium or high stringency.

21. The method of claim 18 wherein the Elovl4 expression system which encodes the ELOVL4 protein comprises an expression control sequence.

22. The method of claim 18 wherein the ELOVL4 protein is at least 95% identical to at least one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

23. The method of claim 18 wherein the unsaturated fatty acid precursor molecule has a structure selected from at least one of 3n3, 4n3, 5n3, 6n3, 7n3 and 8n3.

24. The method of claim 18 wherein the recombinant cell is present in an organism selected from the group consisting of bacteria, fungi, algae, protozoa, plants, and non-human milk-producing animals.

25. The method of claim 18 wherein in the step of culturing the recombinant cell the precursor fatty acid is provided exogenously.

26. A method of producing at least one very long chain polyunsaturated fatty acid (VLC-PUFA) having a chain length of at least 28 carbons, comprising:
providing a recombinant cell which comprises at least one Elovl4 nucleic acid expression system which encodes an ELOVL4 protein which has ELOVL4 elongase activity;
culturing the recombinant cell under conditions effective in causing expression of the ELOVL4 protein wherein the ELOVL4 protein causes elongation of a n6 unsaturated fatty acid precursor molecule having 18-26 carbon atoms to form at least one n6 VLC-PUFA having a chain length of at least 28 carbons in the recombinant cell; and
harvesting the at least one VLC-PUFA from the cultured recombinant cell.

27. The method of claim 26 wherein the chain length of the at least one n6 VLC-PUFA is selected from the group consisting of 28, 30, 32, 34, 36, 38, and 40 carbons.

28. The method of claim 26 wherein the Elovl4 expression system which encodes the ELOVL4 protein comprises a nucleic acid which hybridizes to at least one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO: 17 under conditions of medium or high stringency.

29. The method of claim 26 wherein the Elovl4 expression system which encodes the ELOVL4 protein comprises an expression control sequence.

30. The method of claim 26 wherein the ELOVL4 protein is at least 95% identical to at least one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

31. The method of claim 26 wherein the unsaturated fatty acid precursor molecule has a structure selected from the group consisting of 2n6, 3n6, 4n6, 5n6, 6n6, and 7n6.

32. The method of claim 26 wherein the recombinant cell is present in an organism selected from the group consisting of bacteria, fungi, algae, protozoa, plants, and non-human milk-producing animals.

33. The method of claim 26 wherein in the step of culturing the recombinant cell the precursor fatty acid is provided exogenously.

* * * * *

UNITED STATES PATENT AND TRADEMARK OFFICE
CERTIFICATE OF CORRECTION

| | | |
|---|---|---|
| PATENT NO. | : 8,021,874 B2 | Page 1 of 1 |
| APPLICATION NO. | : 12/361163 | |
| DATED | : September 20, 2011 | |
| INVENTOR(S) | : Robert E. Anderson et al. | |

It is certified that error appears in the above-identified patent and that said Letters Patent is hereby corrected as shown below:

In the Specification:
Column 6, line 57: Delete fingi," and replace with -- fungi, --.

Signed and Sealed this
Eighth Day of November, 2011

David J. Kappos
*Director of the United States Patent and Trademark Office*

SEQUENCE LISTING

```
<160> NUMBER OF SEQ ID NOS: 20

<210> SEQ ID NO 1
<211> LENGTH: 945
<212> TYPE: DNA
<213> ORGANISM: Homo sapiens

<400> SEQUENCE: 1
atggggctcc tggactcgga gccgggtagt gtcctaaacg tagtgtccac ggcactcaac      60
gacacggtag agttctaccg ctggacctgg tccatcgcag ataagcgtgt ggaaaattgg     120
cctctgatgc agtctccttg gcctacacta agtataagca ctctttatct cctgtttgtg    180
tggctgggtc caaaatggat gaaggaccga gaaccttttc agatgcgtct agtgctcatt    240
atctataatt ttgggatggt tttgcttaac ctctttatct tcagagagtt attcatggga    300
tcatataatg cgggatatag ctatatttgc cagagtgtgg attattctaa taatgttcat    360
gaagtcagga tagctgctgc tctgtggtgg tactttgtat ctaaaggagt tgagtatttg    420
gacacagtgt ttttttattct gagaaagaaa acaaccaag tttctttcct tcatgtgtat    480
catcactgta cgatgtttac cttgtggtgg attggaatta agtgggttgc aggaggacaa    540
gcattttttg gagcccagtt gaattccttt atccatgtga ttatgtactc atactatggg    600
ttaactgcat ttggcccatg gattcagaaa tatctttggt ggaaacgata cctgactatg    660
ttgcaactga ttcaattcca tgtgaccatt gggcacacgg cactgtctct ttacactgac    720 tgcccccttcc ccaaatggat gcactgggct ctaattgcct atgcaatcag cttcatattt    780
ctctttctta acttctacat tcggacatac aaagagccta agaaaccaaa agctggaaaa    840
acagccatga atggtatttc agcaaatggt gtgagcaaat cagaaaaaca actcatgata    900
gaaaatggaa aaagcagaa aaatggaaaa gcaaaggag attaa                      945

<210> SEQ ID NO 2
<211> LENGTH: 314
<212> TYPE: PRT
<213> ORGANISM: Homo sapiens

<400> SEQUENCE: 2

Met Gly Leu Leu Asp Ser Glu Pro Gly Ser Val Leu Asn Val Val Ser
1               5                   10                  15

Thr Ala Leu Asn Asp Thr Val Glu Phe Tyr Arg Trp Thr Trp Ser Ile
                20                  25                  30

Ala Asp Lys Arg Val Glu Asn Trp Pro Leu Met Gln Ser Pro Trp Pro
            35                  40                  45

Thr Leu Ser Ile Ser Thr Leu Tyr Leu Leu Phe Val Trp Leu Gly Pro
        50                  55                  60

Lys Trp Met Lys Asp Arg Glu Pro Phe Gln Met Arg Leu Val Leu Ile
65                  70                  75                  80

Ile Tyr Asn Phe Gly Met Val Leu Leu Asn Leu Phe Ile Phe Arg Glu
                85                  90                  95
```

```
Leu Phe Met Gly Ser Tyr Asn Ala Gly Tyr Ser Tyr Ile Cys Gln Ser
            100                 105                 110

Val Asp Tyr Ser Asn Asn Val His Glu Val Arg Ile Ala Ala Ala Leu
            115                 120                 125

Trp Trp Tyr Phe Val Ser Lys Gly Val Glu Tyr Leu Asp Thr Val Phe
        130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Leu Asn Ser Phe Ile His
            180                 185                 190

Val Ile Met Tyr Ser Tyr Tyr Gly Leu Thr Ala Phe Gly Pro Trp Ile
            195                 200                 205

Gln Lys Tyr Leu Trp Trp Lys Arg Tyr Leu Thr Met Leu Gln Leu Ile
        210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Asn Phe Tyr Ile Arg Thr Tyr Lys Glu
            260                 265                 270

Pro Lys Lys Pro Lys Ala Gly Lys Thr Ala Met Asn Gly Ile Ser Ala
        275                 280                 285

Asn Gly Val Ser Lys Ser Glu Leu Gln Leu Met Ile Glu Asn Gly Lys
            290                 295                 300

Lys Gln Lys Asn Gly Lys Ala Lys Gly Asp
305                 310

<210> SEQ ID NO 3
<211> LENGTH: 939
<212> TYPE: DNA
<213> ORGANISM: Mus Musculus

<400> SEQUENCE: 3
atggggctgc tggactcaga gcccggcagc gtcctgaacg cgatgtccac ggcattcaac      60
gacaccgtgg agttctatcg ctggacctgg accattgcag ataaacgtgt agcagactgg     120
ccgctgatgc agtctccatg gccaacgata gcataagca cgctctatct cctgttcgtg     180
tggctgggtc caaagtggat gaagaccgc gagccgttcc aaatgcgctt agtactcata     240
atctataatt ttggcatggt tttgcttaac cttttcatct tcagagagct attcatggga     300
tcatacaacg caggatacag ctatatttgc agtcagtgg attattctaa tgatgttaat     360
gaagtcagga tagcggcggc cctgtggtgg tattttgtat cgaaaggcgt tgagtatttg     420
gacacagtgt tttttatcct gaggaagaaa acaaccaag tctccttcct tcacgtgtac     480
caccactgca ccatgttcac tctgtggtgg attggaatca agtgggtggc tggaggccaa     540
gcgttttcg gggcccagat gaactctttc atccacgtga tcatgtactc ctactatggg     600
ctgactgcgt tcggcccctg gatccagaaa tatctttggt ggaagcgata cctgaccatg     660
ctgcagctgg tccagttcca cgtgaccatc ggacacacag cactgtctct ctacaccgac     720
tgccccttcc ccaagtggat gcactgggct ctgatcgcct acgccatcag cttcatcttc     780
ctcttcctca acttctacac tcggacatac aatgagccga agcagtcaaa accggaaag     840
acggccacga atggtatctc atcgaacggc gtgaataaat cagagaaagc gttagaaaac     900
```
gggaaacccc agaaaaacgg aagccaaaa ggagagtaa                                939

<210> SEQ ID NO 4
<211> LENGTH: 312
<212> TYPE: PRT
<213> ORGANISM: Mus Musculus

<400> SEQUENCE: 4

Met Gly Leu Leu Asp Ser Glu Pro Gly Ser Val Leu Asn Ala Met Ser
1               5                   10                  15

Thr Ala Phe Asn Asp Thr Val Glu Phe Tyr Arg Trp Thr Trp Thr Ile
            20                  25                  30

Ala Asp Lys Arg Val Ala Asp Trp Pro Leu Met Gln Ser Pro Trp Pro
        35                  40                  45

Thr Ile Ser Ile Ser Thr Leu Tyr Leu Leu Phe Val Trp Leu Gly Pro
    50                  55                  60

Lys Trp Met Lys Asp Arg Glu Pro Phe Gln Met Arg Leu Val Leu Ile
65                  70                  75                  80

Ile Tyr Asn Phe Gly Met Val Leu Leu Asn Leu Phe Ile Phe Arg Glu
                85                  90                  95

Leu Phe Met Gly Ser Tyr Asn Ala Gly Tyr Ser Tyr Ile Cys Gln Ser
            100                 105                 110

Val Asp Tyr Ser Asn Asp Val Asn Glu Val Arg Ile Ala Ala Ala Leu
        115                 120                 125

Trp Trp Tyr Phe Val Ser Lys Gly Val Glu Tyr Leu Asp Thr Val Phe
    130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Met Asn Ser Phe Ile His
            180                 185                 190

Val Ile Met Tyr Ser Tyr Tyr Gly Leu Thr Ala Phe Gly Pro Trp Ile
        195                 200                 205

Gln Lys Tyr Leu Trp Trp Lys Arg Tyr Leu Thr Met Leu Gln Leu Val
    210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Asn Phe Tyr Thr Arg Thr Tyr Asn Glu
            260                 265                 270

Pro Lys Gln Ser Lys Thr Gly Lys Thr Ala Thr Asn Gly Ile Ser Ser
        275                 280                 285

Asn Gly Val Asn Lys Ser Glu Lys Ala Leu Glu Asn Gly Lys Pro Gln
    290                 295                 300

Lys Asn Gly Lys Pro Lys Gly Glu
305                 310

<210> SEQ ID NO 5
<211> LENGTH: 945
<212> TYPE: DNA
<213> ORGANISM: Macaca

<400> SEQUENCE: 5
atggggctcc tggactcgga gccgggtagt gtcctaaacg tagtgtccac ggcactcaac    60

-continued

```
gacacggtgg agttctaccg ctggacctgg tccatcgcag ataagcgtgt ggagaattgg      120
cctctgatgc agtctccttg gcctacacta agtataagca ctctttatct cctgtttgtg      180
tggctgggtc caaagtggat gaaggaccga gaaccttttc agatgcgtct agtgctcatt      240
atctataatt ttgggatggt tttgcttaac ttttttatct tcagagagtt attcatggga      300
tcatataatg cgggatatag ctatatttgc cagagtgtgg attattctaa taatgttaat      360
gaagtcagga tagctgctgc tctgtggtgg tactttgttt ctaaaggagt tgagtatttg      420
gacacagtgt tttttattct gagaaagaaa acaaccagg tttctttcct tcatgtgtat       480
catcactgta cgatgtttac cttgtggtgg attggaatta agtgggttgc aggaggacaa      540 gcatttttg gagcccagat gaattccttt atccatgtga ttatgtactc atactatggg       600
ttagctgcat ttggcccatg gattcagaaa tatctttggt ggaaacgata cctgactatg      660
ttgcaactgg ttcaattcca tgtgaccatt gggcacacag cactgtctct ttacactgac      720
tgccccttcc ccaaatggat gcactgggct ctaattgcct acgcaatcag cttcatattt      780
ctctttctta acttctacat tcggacatac aaagagccta agaaaccaaa aactggaaaa      840
acagccatga atggtatttc agcaaatggt gtgagcaaat cagaaaaaca actcgtgata      900
gaaaacggaa aaagcagaa aaatggaaaa gcaaaggag attaa                        945
```

<210> SEQ ID NO 6
<211> LENGTH: 314
<212> TYPE: PRT
<213> ORGANISM: Macaca
<400> SEQUENCE: 6

```
Met Gly Leu Leu Asp Ser Glu Pro Gly Ser Val Leu Asn Val Ser
1               5                   10                  15

Thr Ala Leu Asn Asp Thr Val Glu Phe Tyr Arg Trp Thr Trp Ser Ile
                20                  25                  30

Ala Asp Lys Arg Val Glu Asn Trp Pro Leu Met Gln Ser Pro Trp Pro
            35                  40                  45

Thr Leu Ser Ile Ser Thr Leu Tyr Leu Leu Phe Val Trp Leu Gly Pro
        50                  55                  60

Lys Trp Met Lys Asp Arg Glu Pro Phe Gln Met Arg Leu Val Leu Ile
65                  70                  75                  80

Ile Tyr Asn Phe Gly Met Val Leu Leu Asn Phe Ile Phe Arg Glu
                85                  90                  95

Leu Phe Met Gly Ser Tyr Asn Ala Gly Tyr Ser Tyr Ile Cys Gln Ser
            100                 105                 110

Val Asp Tyr Ser Asn Asn Val Asn Glu Val Arg Ile Ala Ala Ala Leu
        115                 120                 125

Trp Trp Tyr Phe Val Ser Lys Gly Val Glu Tyr Leu Asp Thr Val Phe
    130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Met Asn Ser Phe Ile His
            180                 185                 190

Val Ile Met Tyr Ser Tyr Tyr Gly Leu Ala Ala Phe Gly Pro Trp Ile
        195                 200                 205

Gln Lys Tyr Leu Trp Trp Lys Arg Tyr Leu Thr Met Leu Gln Leu Val
    210                 215                 220
```

```
Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
            245                 250                 255

Ser Phe Ile Phe Leu Phe Leu Asn Phe Tyr Ile Arg Thr Tyr Lys Glu
        260                 265                 270

Pro Lys Lys Pro Lys Thr Gly Lys Thr Ala Met Asn Gly Ile Ser Ala
    275                 280                 285

Asn Gly Val Ser Lys Ser Glu Lys Gln Leu Val Ile Glu Asn Gly Lys
    290                 295                 300

Lys Gln Lys Asn Gly Lys Ala Lys Gly Asp
305                 310

<210> SEQ ID NO 7
<211> LENGTH: 945
<212> TYPE: DNA
<213> ORGANISM: Bos taurus

<400> SEQUENCE: 7
atggggctcc tggactcgga gccgggcagc gtcctgaacg cggtgtccac ggcgctgaac      60
gacaccgtgg agttctaccg ctggaccttg tccatcacag ataaacgcgt cgagaactgg     120
cctctgatgc agtctccact gcctacactt tgcataagca ccctgtacct cctcttcgtg     180
tggctgggtc caaaatggat gaaggaccga gaacctttcc agatgcgttt agtgctcatt     240
ctctataatt tcgggatggt tttgcttaac ctttttatct tcagagagtt actcatggga     300
tcatataatg caggatatag ctatatttgc cagactgtgg attattctga taacgttcat     360
gaagtcagga tagctgctgc tctgtggtgg tactttatat ctaaaggaat tgagtatttg     420
gacacggtgt tttttatcct gaggaagaaa aacaaccaag tctctttttct tcacgtgtat     480 catcactgta ccatgtttac gttgtggtgg attggaatta gtgggttgca aggaggacag     540 gcatttttg agcccagat aaattccttc atccatgtga ttatgtattc atactatggg     600
ttagctgcct tcggcccgtg gattcagaaa tatctctggt ggaaacgata cctgaccatg     660
ttgcagctgg ttcagttcca cgtgaccatt gggcacacag cactgtccct ttacaccgac     720
tgccccttcc ccaagtggat gcactgggct ctcattgtct atgcagtcag cttcatattc     780
ctcttcctta acttctatgt gcggacgtac aaagagccta gaaagcaaa acccggaaaa     840 acagcaacga atggtatttc agctaatggt gtgaacaaat ccgaaaacca cctagtggta     900
gaaaatggca agaagcagaa gaatggaaaa gcaaaggag agtaa                      945

<210> SEQ ID NO 8
<211> LENGTH: 314
<212> TYPE: PRT
<213> ORGANISM: Bos taurus

<400> SEQUENCE: 8

Met Gly Leu Leu Asp Ser Glu Pro Gly Ser Val Leu Asn Ala Val Ser
1               5                   10                  15

Thr Ala Leu Asn Asp Thr Val Glu Phe Tyr Arg Trp Thr Leu Ser Ile
            20                  25                  30

Thr Asp Lys Arg Val Glu Asn Trp Pro Leu Met Gln Ser Pro Leu Pro
        35                  40                  45

Thr Leu Cys Ile Ser Thr Leu Tyr Leu Leu Phe Val Trp Leu Gly Pro
    50                  55                  60

Lys Trp Met Lys Asp Arg Glu Pro Phe Gln Met Arg Leu Val Leu Ile
65                  70                  75                  80
```

Leu Tyr Asn Phe Gly Met Val Leu Leu Asn Leu Phe Ile Phe Arg Glu
                85                  90                  95
Leu Leu Met Gly Ser Tyr Asn Ala Gly Tyr Ser Tyr Ile Cys Gln Thr
            100                 105                 110
Val Asp Tyr Ser Asp Asn Val His Glu Val Arg Ile Ala Ala Ala Leu
        115                 120                 125
Trp Trp Tyr Phe Ile Ser Lys Gly Ile Glu Tyr Leu Asp Thr Val Phe
    130                 135                 140
Phe Ile Leu Arg Lys Lys Asn Asn Gln Val Ser Phe Leu His Val Tyr
145                 150                 155                 160
His His Cys Thr Met Phe Thr Leu Trp Trp Ile Gly Ile Lys Trp Val
                165                 170                 175
Ala Gly Gly Gln Ala Phe Phe Gly Ala Gln Ile Asn Ser Phe Ile His
            180                 185                 190
Val Ile Met Tyr Ser Tyr Tyr Gly Leu Ala Ala Phe Gly Pro Trp Ile
        195                 200                 205
Gln Lys Tyr Leu Trp Trp Lys Arg Tyr Leu Thr Met Leu Gln Leu Val
    210                 215                 220
Gln Phe His Val Thr Ile Gly His Thr Ala Leu Ser Leu Tyr Thr Asp
225                 230                 235                 240
Cys Pro Phe Pro Lys Trp Met His Trp Ala Leu Ile Val Tyr Ala Val
                245                 250                 255
Ser Phe Ile Phe Leu Phe Leu Asn Phe Tyr Val Arg Thr Tyr Lys Glu
            260                 265                 270
Pro Lys Lys Ala Lys Pro Gly Lys Thr Ala Thr Asn Gly Ile Ser Ala
        275                 280                 285
Asn Gly Val Asn Lys Ser Glu Asn His Leu Val Val Glu Asn Gly Lys
    290                 295                 300
Lys Gln Lys Asn Gly Lys Ala Lys Gly Glu
305                 310

<210> SEQ ID NO 9
<211> LENGTH: 945
<212> TYPE: DNA
<213> ORGANISM: Equus caballus

<400> SEQUENCE: 9
atggggctcc tggacgcgga gccaggcagt gtcctgaacg tggtgtccac ggcgctcaac      60
gacaccgtgg agttgtaccg ctggacctgt tctttcgcag ataagcgtgt ggaaaactgg     120
cctctgatgc agtccccatg gactacgctt ggtatcagca ctctttatct cctgttcgtg     180
tggctgggtc aaaatggat gaaggaccga gagccttttc agatgcgctt agtgctcatt     240
atctataatt ttggcatggt tttccttaac cttttatct tcagagagtt attcatggga     300
tcatataatg caggatatag ctatatttgc cagactgtgg attattctga atatgttcac     360
gaagtcagga tagctgctgc tctgtggtgg tactttgtgt ctaaaggagt ggagtattta     420
gacacggtgt tttttatctt gaggaagaaa acaatcaag tctctttcct tcatgtatat     480
catcactgta caatgtttac gttgtggtgg attggaatta gtgggtcgc aggggggacaa     540 gcttttttcg gagcccagat gaattccctc atccatgtga ttatgtactc ctactacggc     600
ttaagtgcgt ttggcccatg gattcagaag tatctttggt ggaaacgata cctgactatg     660
ttgcagctga tccagttcca tgtgaccatt ggccacacag cactgtctct gtacacggat     720 tgcccctttcc ccaaatggat gcactgggct ctcattgtct attcaatcag cttcatactt     780

```
ctctttctta acttctatgt tcggacatac aacatgccta agaaatccca aactggaaaa      840
ccagctgtga atggtatttc agcaaatggt gtgagcaaat cagaaaaaca gctagtgatg      900
gaaaatggaa aaaagcagaa aactggaaaa gcaaaaggag agtaa                     945
```

<210> SEQ ID NO 10
<211> LENGTH: 314
<212> TYPE: PRT
<213> ORGANISM: Equus caballus

<400> SEQUENCE: 10

```
Met Gly Leu Leu Asp Ala Glu Pro Gly Ser Val Leu Asn Val Ser
1               5                   10                  15

Thr Ala Leu Asn Asp Thr Val Glu Leu Tyr Arg Trp Thr Cys Ser Phe
            20                  25                  30

Ala Asp Lys Arg Val Glu Asn Trp Pro Leu Met Gln Ser Pro Trp Thr
        35                  40                  45

Thr Leu Gly Ile Ser Thr Leu Tyr Leu Phe Val Trp Leu Gly Pro
    50                  55                  60

Lys Trp Met Lys Asp Arg Glu Pro Phe Gln Met Arg Leu Val Leu Ile
65                  70                  75                  80

Ile Tyr Asn Phe Gly Met Val Phe Leu Asn Leu Phe Ile Phe Arg Glu
                85                  90                  95

Leu Phe Met Gly Ser Tyr Asn Ala Gly Tyr Ser Tyr Ile Cys Gln Thr
            100                 105                 110

Val Asp Tyr Ser Asp Asn Val His Glu Val Arg Ile Ala Ala Ala Leu
        115                 120                 125

Trp Trp Tyr Phe Val Ser Lys Gly Val Glu Tyr Leu Asp Thr Val Phe
    130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Met Asn Ser Leu Ile His
            180                 185                 190

Val Ile Met Tyr Ser Tyr Tyr Gly Leu Ser Ala Phe Gly Pro Trp Ile
        195                 200                 205

Gln Lys Tyr Leu Trp Trp Lys Arg Tyr Leu Thr Met Leu Gln Leu Ile
    210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Val Tyr Ser Ile
                245                 250                 255

Ser Phe Ile Leu Leu Phe Leu Asn Phe Tyr Val Arg Thr Tyr Asn Met
            260                 265                 270

Pro Lys Lys Ser Gln Thr Gly Lys Pro Ala Val Asn Gly Ile Ser Ala
        275                 280                 285

Asn Gly Val Ser Lys Ser Glu Lys Gln Leu Val Met Glu Asn Gly Lys
    290                 295                 300

Lys Gln Lys Thr Gly Lys Ala Lys Gly Glu
305                 310
```

<210> SEQ ID NO 11
<211> LENGTH: 945
<212> TYPE: DNA
<213> ORGANISM: Gallus gallus

<400> SEQUENCE: 11

```
atgggtgccg ccgccgccga gccccccgc gccgcgggcc tggtgtccag cgtgctgaac      60
gacaccctcg agttctaccg ctggacctgg agcatccgag acaaacgtgt cgatgattgg     120
cccttgatgc agtctccatt tccaacactg actataagca ctatttatct cctcactgtt    180
tggctgggcc ccaaatggat gaagacaaga gagcccttcc agttacgttt cctgttggtt    240
gtttacaact ttggaatggt tctactcaac ttcttcattt tcaaagagct gttttatca     300
tcaagagctc gagggtacag ctatgtctgc cagactgtgg attattcaga taatgtttat    360
gaagttagga tagctgctgc tttatggtgg tattatgtct ccaaaggaat gaataccta     420
gatacagtct tcttcatcct gaggaagaag ttcaaccaaa ttagttttct tcatgtctat    480
caccatttca ccatgttcac tttgtggtgg attggtatta gtgggttgc aggtggacaa     540
gcttttttg gagctcagat gaatgcattt attcatgtta ttatgtacat gtattacgga    600
ttagctgcct gtggccctaa agttcagaag tatctgtggt ggaaacgata cttgactata    660
ttgcaactgg tgcagttcca tgtgactatt ggccacacag ccttgtctat ttatatcgat    720
tgtcctttcc ctaaatggat gcactggggt gtaattttct atgctatcac cttcattttc    780
ttgtttggta acttctacta tcggacatat aagctgccca aggaacctgt aaagaatggc    840
aaaatagcaa atggtgctgt tgcaaacgga gtaagcaaac cagaaaataa tccagtggtg    900
gaaaatggaa aaaagcagaa aaagggaaaa gcaaaggag agtaa                     945
```

<210> SEQ ID NO 12
<211> LENGTH: 313
<212> TYPE: PRT
<213> ORGANISM: Gallus gallus

<400> SEQUENCE: 12

```
Met Gly Ala Ala Ala Glu Pro Pro Arg Ala Ala Gly Leu Val Ser
1               5                   10                  15

Ser Val Leu Asn Asp Thr Leu Glu Phe Tyr Arg Trp Thr Trp Ser Ile
                20                  25                  30

Arg Asp Lys Arg Val Asp Asp Trp Pro Leu Met Gln Ser Pro Phe Pro
            35                  40                  45

Thr Leu Thr Ile Ser Thr Ile Tyr Leu Leu Thr Val Trp Leu Gly Pro
        50                  55                  60

Lys Trp Met Lys Thr Arg Glu Pro Phe Gln Leu Arg Phe Leu Leu Val
65                  70                  75                  80

Val Tyr Asn Phe Gly Met Val Leu Leu Asn Phe Ile Phe Lys Glu
                85                  90                  95

Leu Phe Leu Ser Ser Arg Arg Gly Tyr Ser Tyr Val Cys Gln Thr Val
                100                 105                 110

Asp Tyr Ser Asp Asn Val Tyr Glu Val Arg Ile Ala Ala Ala Leu Trp
            115                 120                 125

Trp Tyr Tyr Val Ser Lys Gly Ile Glu Tyr Leu Asp Thr Val Phe Phe
        130                 135                 140

Ile Leu Arg Lys Lys Phe Asn Gln Ile Ser Phe Leu His Val Tyr His
145                 150                 155                 160

His Phe Thr Met Phe Thr Leu Trp Trp Ile Gly Ile Lys Trp Val Ala
                165                 170                 175

Gly Gly Gln Ala Phe Phe Gly Ala Gln Met Asn Ala Phe Ile His Val
            180                 185                 190

Ile Met Tyr Met Tyr Tyr Gly Leu Ala Ala Cys Gly Pro Lys Val Gln
        195                 200                 205
```

```
Lys Tyr Leu Trp Trp Lys Arg Tyr Leu Thr Ile Leu Gln Leu Val Gln
    210                 215                 220

Phe His Val Thr Ile Gly His Thr Ala Leu Ser Ile Tyr Ile Asp Cys
225                 230                 235                 240

Pro Phe Pro Lys Trp Met His Trp Gly Val Ile Phe Tyr Ala Ile Thr
                245                 250                 255

Phe Ile Phe Leu Phe Gly Asn Phe Tyr Tyr Arg Thr Tyr Lys Leu Pro
                260                 265                 270

Lys Glu Pro Val Lys Asn Gly Lys Ile Ala Asn Gly Val Ala Asn
        275                 280                 285

Gly Val Ser Lys Pro Glu Asn Asn Pro Val Val Glu Asn Gly Lys Lys
    290                 295                 300

Gln Lys Lys Gly Lys Ala Lys Gly Glu
305                 310

<210> SEQ ID NO 13
<211> LENGTH: 912
<212> TYPE: DNA
<213> ORGANISM: Danio rerio

<400> SEQUENCE: 13
atggagacgg tcgttcacct gatgaatgac tctgtagagt tttacaaatg gagccttacc    60
atagcagaca agcgtgtgga gaaatggccg atgatgtcat ctcctctgcc cactctgggg   120
atcagtgttt tgtacctgct cttcctttgg gccggccctc tttacatgca gaaccgcgag   180
cctttccagc tcaggaaaac actcattgtg tacaacttca gcatggtgct gcttaacttc   240
tacatctgca aagagctgct cctgggctcc agagcagccg atacagcta cctctgccag    300 cctgtcaact actccaatga tgttaatgaa gtcaggatag catctgctct gtggtggtat   360
tacatctcca agggagtgga gtttctggac acggtcttct tcatcatgag gaagaagttt   420
aatcaggtca gcttcctgca cgtctatcac cactgcacaa tgttcatcct gtggtggatc   480
ggcatcaagt gggttcctgg tggacagtct ttctttggcg caacgattaa ctcaggcatt   540
catgtgctga tgtacggcta ctacggcctg cagcgtttg ccccgaagat ccagaagtac    600
ctgtggtgga agaaatacct cactattatt cagatgatcc agttccacgt caccattggc   660
catgctgctc actctctcta cacgggctgt ccattcccag catggatgca gtgggctttg   720
attggctatg ccgttacatt catcatcctg ttcgccaatt tttactacca gacctaccgt   780
cgccagccac gtctcaagac agccaaatcc gcagttaacg gcgtctccat gtcaaccaac   840
ggcaccagca agacagccga ggtcacggaa atggaaaga acagaagaa ggaaaagga     900 aagcacgatt aa                                                      912

<210> SEQ ID NO 14
<211> LENGTH: 303
<212> TYPE: PRT
<213> ORGANISM: Danio rerio

<400> SEQUENCE: 14

Met Glu Thr Val Val His Leu Met Asn Asp Ser Val Glu Phe Tyr Lys
1               5                   10                  15

Trp Ser Leu Thr Ile Ala Asp Lys Arg Val Glu Lys Trp Pro Met Met
            20                  25                  30

Ser Ser Pro Leu Pro Thr Leu Gly Ile Ser Val Leu Tyr Leu Leu Phe
        35                  40                  45

Leu Trp Ala Gly Pro Leu Tyr Met Gln Asn Arg Glu Pro Phe Gln Leu
```

```
              50                  55                  60
Arg Lys Thr Leu Ile Val Tyr Asn Phe Ser Met Val Leu Leu Asn Phe
 65                  70                  75                  80

Tyr Ile Cys Lys Glu Leu Leu Leu Gly Ser Arg Ala Ala Gly Tyr Ser
                 85                  90                  95

Tyr Leu Cys Gln Pro Val Asn Tyr Ser Asn Asp Val Asn Glu Val Arg
                100                 105                 110

Ile Ala Ser Ala Leu Trp Trp Tyr Tyr Ile Ser Lys Gly Val Glu Phe
            115                 120                 125

Leu Asp Thr Val Phe Phe Ile Met Arg Lys Lys Phe Asn Gln Val Ser
130                 135                 140

Phe Leu His Val Tyr His His Cys Thr Met Phe Ile Leu Trp Trp Ile
145                 150                 155                 160

Gly Ile Lys Trp Val Pro Gly Gly Gln Ser Phe Gly Ala Thr Ile
                165                 170                 175

Asn Ser Gly Ile His Val Leu Met Tyr Gly Tyr Tyr Gly Leu Ala Ala
            180                 185                 190

Phe Gly Pro Lys Ile Gln Lys Tyr Leu Trp Trp Lys Lys Tyr Leu Thr
        195                 200                 205

Ile Ile Gln Met Ile Gln Phe His Val Thr Ile Gly His Ala Ala His
210                 215                 220

Ser Leu Tyr Thr Gly Cys Pro Phe Pro Ala Trp Met Gln Trp Ala Leu
225                 230                 235                 240

Ile Gly Tyr Ala Val Thr Phe Ile Ile Leu Phe Ala Asn Phe Tyr Tyr
                245                 250                 255

Gln Thr Tyr Arg Arg Gln Pro Arg Leu Lys Thr Ala Lys Ser Ala Val
                260                 265                 270

Asn Gly Val Ser Met Ser Thr Asn Gly Thr Ser Lys Thr Ala Glu Val
            275                 280                 285

Thr Glu Asn Gly Lys Lys Gln Lys Gly Lys Gly Lys His Asp
        290                 295                 300
```

<210> SEQ ID NO 15
<211> LENGTH: 660
<212> TYPE: DNA
<213> ORGANISM: Xenopus

<400> SEQUENCE: 15

```
atgaagtcag gctggcctca gctctctggt ggtactatgt ttcaaaaggg gtggaatatt      60
ttgacacagt attttcata cttagaaaaa aaattcaacc aaattagttt tctgcatgta     120
tatcaccact gcacaatgtt cacactctgg tggatcggaa tcaaatgggt tgccggagga    180
caatcatttt ttggagcgca catgaatgca ctgatccatg ttgtgatgta cttatattat    240
gggttggctg cctgtggacc acatctacag aagtatttat ggtggaaacg atatctgaca    300
atattgcagc tggttcaatt ccatgtgaca atcggacata cagctttatc actgtacatt    360
gattgtccat ttcccaagtg gatgcattgg gctctgattg tgtatgctat cactttatt     420
attcttttcg ttaacttcta ctaccggaca tacaatgctc ccaaagcacc agctaaaagt    480
gggaaatcac tcataaatgg aaagacctct gttaatggca agtcctctgt gaatggaaaa    540
tgccaaatta tgaaaaatt aatgaatgga gcagttaatg agctgtaag caagcaagat     600
aataaagttg acaagaaaaa tgggcgaaaa aggagaaaag gaagagccaa gcgagaataa    660
```

<210> SEQ ID NO 16
<211> LENGTH: 219

<210> TYPE: PRT
<213> ORGANISM: Xenopus

<400> SEQUENCE: 16

```
Met Lys Ser Gly Trp Pro Gln Leu Ser Gly Gly Thr Met Phe Gln Lys
1               5                   10                  15

Gly Trp Asn Ile Leu Thr Gln Tyr Phe Ser Tyr Leu Glu Lys Lys Phe
            20                  25                  30

Asn Gln Ile Ser Phe Leu His Val Tyr His His Cys Thr Met Phe Thr
        35                  40                  45

Leu Trp Trp Ile Gly Ile Lys Trp Val Ala Gly Gln Ser Phe Phe
    50                  55                  60

Gly Ala His Met Asn Ala Leu Ile His Val Val Met Tyr Leu Tyr Tyr
65                  70                  75                  80

Gly Leu Ala Ala Cys Gly Pro His Leu Gln Lys Tyr Leu Trp Trp Lys
                85                  90                  95

Arg Tyr Leu Thr Ile Leu Gln Leu Val Gln Phe His Val Thr Ile Gly
            100                 105                 110

His Thr Ala Leu Ser Leu Tyr Ile Asp Cys Pro Phe Pro Lys Trp Met
        115                 120                 125

His Trp Ala Leu Ile Val Tyr Ala Ile Thr Phe Ile Ile Leu Phe Val
    130                 135                 140

Asn Phe Tyr Tyr Arg Thr Tyr Asn Ala Pro Lys Ala Pro Ala Lys Ser
145                 150                 155                 160

Gly Lys Ser Leu Ile Asn Gly Lys Thr Ser Val Asn Gly Lys Ser Ser
                165                 170                 175

Val Asn Gly Lys Cys Gln Ile Asn Gly Lys Leu Met Asn Gly Ala Val
            180                 185                 190

Asn Gly Ala Val Ser Lys Gln Asp Asn Lys Val Gly Gln Glu Asn Gly
        195                 200                 205

Arg Lys Arg Arg Lys Gly Arg Ala Lys Arg Glu
    210                 215
```

<210> SEQ ID NO 17
<211> LENGTH: 1038
<212> TYPE: DNA
<213> ORGANISM: Yeast

<400> SEQUENCE: 17

| | | | | |
|---|---|---|---|---|
| atgaacacta ccacatctac tgttatagca gcagttgccg accagttcca gtctttgaac | 60 |
| tcttcttctt catgtttctt gaaggttcat gttccttcca ttgagaaccc attcggtatt | 120 |
| gaattatggc caattttctc caaagtgttt gaatacttta gtggctatcc agctgagcaa | 180 |
| ttcgagttta ttcacaataa gactttcttg gctaacgggt atcatgctgt tagtattatt | 240 |
| atcgtttatt acattattat ctttggtggc caagctatct tacgcgcctt gaacgcctct | 300 |
| ccattaaagt ttaaattgct tttcgagata cacaacttgt ttttgacttc tatttctcta | 360 |
| gttttatggt tgctgatgtt agaacagttg gttcctatgg tttatcacaa cggtctattc | 420 |
| tggtctatct gctctaagga agccttcgca ccaaaattag ttactcttta ctatttgaac | 480 |
| tatttgacca aattcgtaga attgattgac actgtgtttt agttttgag aagaaagaag | 540 |
| ttattgtttt tgcacactta ccatcacggt gccaccgctt gttgtgcta cactcaatta | 600 |
| attggtcgta cttctgttga atgggtagtt atcctactaa acttgggtgt tcacgttatc | 660 |
| atgtactggt actacttctt gagttcatgt ggtattagag tttggtggaa gcaatgggtc | 720 |
| actagattcc aaattattca atttttgatt gacttggtat ttgtttactt tgctacctat | 780 |

```
acattctatg ctcacaaata cttggacggt attttaccaa acaagggtac ttgttatggt    840
actcaggctg ctgctgctta tgggtatttg attctaacat cttatttgct tttgtttatt    900
tccttctaca tccaatctta caagaaaggt ggtaaaaaga cagtcaagaa ggaatctgaa    960
gtttccggct ccgttgcatc cggttcttct actggtgtca agacctctaa caccaaggtc   1020
tcttccagga aagcttaa                                                 1038

<210> SEQ ID NO 18
<211> LENGTH: 345
<212> TYPE: PRT
<213> ORGANISM: Yeast

<400> SEQUENCE: 18

Met Asn Thr Thr Thr Ser Thr Val Ile Ala Ala Val Ala Asp Gln Phe
1               5                   10                  15

Gln Ser Leu Asn Ser Ser Ser Cys Phe Leu Lys Val His Val Pro
            20                  25                  30

Ser Ile Glu Asn Pro Phe Gly Ile Glu Leu Trp Pro Ile Phe Ser Lys
        35                  40                  45

Val Phe Glu Tyr Phe Ser Gly Tyr Pro Ala Glu Gln Phe Glu Phe Ile
    50                  55                  60

His Asn Lys Thr Phe Leu Ala Asn Gly Tyr His Ala Val Ser Ile Ile
65                  70                  75                  80

Ile Val Tyr Tyr Ile Ile Ile Phe Gly Gly Gln Ala Ile Leu Arg Ala
                85                  90                  95

Leu Asn Ala Ser Pro Leu Lys Phe Lys Leu Leu Phe Glu Ile His Asn
            100                 105                 110

Leu Phe Leu Thr Ser Ile Ser Leu Val Leu Trp Leu Leu Met Leu Glu
        115                 120                 125

Gln Leu Val Pro Met Val Tyr His Asn Gly Leu Phe Trp Ser Ile Cys
    130                 135                 140

Ser Lys Glu Ala Phe Ala Pro Lys Leu Val Thr Leu Tyr Tyr Leu Asn
145                 150                 155                 160

Tyr Leu Thr Lys Phe Val Glu Leu Ile Asp Thr Val Phe Leu Val Leu
                165                 170                 175

Arg Arg Lys Lys Leu Leu Phe Leu His Thr Tyr His His Gly Ala Thr
            180                 185                 190

Ala Leu Leu Cys Tyr Thr Gln Leu Ile Gly Arg Thr Ser Val Glu Trp
        195                 200                 205

Val Val Ile Leu Leu Asn Leu Gly Val His Val Ile Met Tyr Trp Tyr
    210                 215                 220

Tyr Phe Leu Ser Ser Cys Gly Ile Arg Val Trp Trp Lys Gln Trp Val
225                 230                 235                 240

Thr Arg Phe Gln Ile Ile Gln Phe Leu Ile Asp Leu Val Phe Val Tyr
                245                 250                 255

Phe Ala Thr Tyr Thr Phe Tyr Ala His Lys Tyr Leu Asp Gly Ile Leu
            260                 265                 270

Pro Asn Lys Gly Thr Cys Tyr Gly Thr Gln Ala Ala Ala Ala Tyr Gly
        275                 280                 285

Tyr Leu Ile Leu Thr Ser Tyr Leu Leu Phe Ile Ser Phe Tyr Ile
    290                 295                 300

Gln Ser Tyr Lys Lys Gly Gly Lys Lys Thr Val Lys Lys Glu Ser Glu
305                 310                 315                 320

Val Ser Gly Ser Val Ala Ser Gly Ser Ser Thr Gly Val Lys Thr Ser
```

```
                    325                 330                 335
Asn Thr Lys Val Ser Ser Arg Lys Ala
                340                 345

<210> SEQ ID NO 19
<211> LENGTH: 5
<212> TYPE: PRT
<213> ORGANISM: Artificial
<220> FEATURE:
<223> OTHER INFORMATION: Completely synthesized.
<220> FEATURE:
<221> NAME/KEY: MISC_FEATURE
<222> LOCATION: (2)..(2)
<223> OTHER INFORMATION: Xaa at position 2 is gly, ala, val, leu, ile,
      met, phe, pro, ser, thr, cys, asn, gln, tyr, trp, asp, glu, his,
      lys, arg.
<220> FEATURE:
<221> NAME/KEY: MISC_FEATURE
<222> LOCATION: (4)..(4)
<223> OTHER INFORMATION: Xaa at position 4 is gly, ala, val, leu, ile,
      met, phe, pro, ser, thr, cys, asn, gln, tyr, trp, asp, glu, his,
      lys, arg.
<220> FEATURE:
<221> NAME/KEY: MISC_FEATURE
<222> LOCATION: (5)..(5)
<223> OTHER INFORMATION: Xaa at position 5 is gly, ala, val, leu, ile,
      met, phe, pro, ser, thr, cys, asn, gln, tyr, trp, asp, glu, his,
      lys, arg.

<400> SEQUENCE: 19

Lys Xaa Lys Xaa Xaa
1               5

<210> SEQ ID NO 20
<211> LENGTH: 5
<212> TYPE: PRT
<213> ORGANISM: Artificial
<220> FEATURE:
<223> OTHER INFORMATION: Completely synthesized.
<220> FEATURE:
<221> NAME/KEY: MISC_FEATURE
<222> LOCATION: (2)..(2)
<223> OTHER INFORMATION: Xaa at position 2 is gly, ala, val, leu, ile,
      met, phe, pro, ser, thr, cys, asn, gln, tyr, trp, asp, glu, his,
      lys, arg.
<220> FEATURE:
<221> NAME/KEY: MISC_FEATURE
<222> LOCATION: (3)..(3)
<223> OTHER INFORMATION: Xaa at position 3 is gly, ala, val, leu, ile,
      met, phe, pro, ser, thr, cys, asn, gln, tyr, trp, asp, glu, his,
      lys, arg.

<400> SEQUENCE: 20

His Xaa Xaa His His
1               5
```